(12) United States Patent
Waehaelae et al.

(10) Patent No.: US 7,754,709 B2
(45) Date of Patent: Jul. 13, 2010

(54) TETRACYCLIC THIOPHENEPYRIMIDINONE COMPOUNDS AS INHIBITORS OF 17β HYDROXYSTEROID DEHYDROGENASE COMPOUNDS

(75) Inventors: Kristiina Waehaelae, Helsinki (FI); Annamaria Lilienkampf, Helsinki (FI); Sari Alho, Menkijaervi (FI); Kaisa Huhtinen, Turku (FI); Nina Johansson, Turku (FI); Pasi Koskimies, Turku (FI); Kimmo Vihko, Turku (FI)

(73) Assignee: Solvay Pharmaceuticals BV, Weesp (NL)

( * ) Notice: Subject to any disclaimer, the term of this patent is extended or adjusted under 35 U.S.C. 154(b) by 815 days.

(21) Appl. No.: 10/861,922

(22) Filed: Jun. 7, 2004

(65) Prior Publication Data

US 2005/0032778 A1 Feb. 10, 2005

Related U.S. Application Data

(60) Provisional application No. 60/477,017, filed on Jun. 10, 2003.

(51) Int. Cl.
| | |
|---|---|
| A61K 31/55 | (2006.01) |
| A61K 31/4985 | (2006.01) |
| A61K 31/519 | (2006.01) |
| A61P 35/04 | (2006.01) |
| A61P 7/04 | (2006.01) |
| A61P 19/10 | (2006.01) |
| A61P 15/10 | (2006.01) |
| A61P 5/24 | (2006.01) |
| C07D 223/04 | (2006.01) |
| C07D 487/04 | (2006.01) |

(52) U.S. Cl. ............... 514/214.02; 514/250; 514/267; 540/476; 540/607; 544/247; 544/343
(58) Field of Classification Search ............ 514/214.02, 514/250, 259.2, 267
See application file for complete search history.

(56) References Cited

U.S. PATENT DOCUMENTS

| 6,541,463 B1 | 4/2003 | Labrie et al. |
| 2003/0170292 A1 | 9/2003 | Yong et al. |

FOREIGN PATENT DOCUMENTS

| DE | 2411273 | * | 9/1975 |
| WO | WO 98/30556 | | 7/1998 |
| WO | WO 98/32724 | | 7/1998 |
| WO | WO 99/12540 | | 3/1999 |
| WO | WO 00/07998 | | 2/2000 |
| WO | WO 01/42181 | | 6/2001 |
| WO | WO 02/26706 | | 4/2002 |
| WO | WO 03/017973 A1 | | 3/2003 |
| WO | WO 03/022835 | | 3/2003 |
| WO | WO 2004/080271 A2 | | 9/2004 |

OTHER PUBLICATIONS

Nonsteroidal anti-inflammatory drugs (NSAIDs) for prostatitis (http://health.yahoo.com/ency/healthwise/aa140761), downloaded Feb. 2, 2007.*
Endometriosis (http://www.umm.edu/altmed/ConsConditions/Endometriosiscc.html), downloaded Feb. 3, 2007.*
Kapustina et. al. (Khimiko-Farmatsevticheskii Zhurnal, 1992, 26(1), 56-57).*
Seborrhea, Seborrheic Dermatitis (http://dermatology.about.com/cs/seborrhea/a/sebderm.htm), dowloaded Feb. 3, 2007.*
CAS print out, 3 pages.*
Stefan Andersson, "Molecular Genetics of Androgenic 17β-Hydroxysteroid Dehydrogenases", J. Steroid Biochem. Molec. Biol., 1995, pp. 533-534, vol. 55, No. 5/6, Elsevier Science Ltd., Great Britain.
Fernand Labrie et al., "The Key Role of 17 β-Hydroxysteroid Dehydrogenases in Sex Steroid Biology", Steroids, Jan. 1997, pp. 148-158, vol. 62, Elsevier Science Ltd., New York, New York, USA.
Donald Poirier, "Inhibitors of 17 β-Hydroxysteroid Dehydrogenases", Current Medicinal Chemistry, 2003, pp. 453-477, vol. 10, No. 6, 2003 Bentham Science Publishers Ltd.
T. Tamaya et al., "Comparison of Cellular Levels of Steroid Receptors in Uterine Leiomyoma and Myometrium", Acta Obstet Gynecol Scand, 1985, pp. 307-309, 64.
Yu Dong et al., "17 β-Hydroxysteroid Dehydrogenases in Human Bone Cells", Journal of Bone and Mineral Research, 1998, pp. 1539-1546, vol. 13, No. 10, American Society for Bone and Mineral Research.
Fernand Labrie et al., "Role of 17 β-Hydroxysteroid Dehydrogenases in Sex Steroid Formation in Peripheral Intracrine Tissues", TEM, 2000, pp. 421-427, vol. 11, No. 10, Elsevier Science Ltd.
M.S. Manhas et al., "Heterocyclic Compounds 4. Synthesis and Antiinflammatory Activity of Some Substituted Thienopyrimidones", Journal of Medicinal Chemistry, pp. 106-107, vol. 15, No. 1, 1972.
Michael G. Oefelein et al., "Failure to Achieve Castrate Levels of Testosterone During Luteinizing Hormone Releasing Hormone Agonist Therapy: The Case for Monitoring Serum Testosterone and a Treatment Decision Algorithm", The Journal of Urology, Sep. 2000, pp. 726-729, vol. 164, American Urological Association, Inc., USA.
B. Koffman et al. "Evidence for Involvement of Tyrosine in Estradiol Binding by Rat Uterus Estrogen Receptor", J. Steroid Biochem. Molec. Biol., 1991, pp. 135-139, vol. 38, No. 2, Pergamon Press plc., Great Britain.
Wayne M. Geissler et al., "Male Pseudohermaphroditism Caused by Mutations of Testicular 17 β-Hydroxysteroid Dehydrogenase 3", Nature Genetics, May 1994, pp. 34-39, vol. 7.

(Continued)

*Primary Examiner*—Susanna Moore
(74) *Attorney, Agent, or Firm*—Crowell & Moring, LLP

(57) ABSTRACT

Thiophenepyrmidinone compounds useful in therapy, especially for use in the treatment and/or prevention of a steroid hormone dependent disorder, preferably a steroid hormone dependent disease or disorder requiring the inhibition of a 17β-hydroxysteroid dehydrogenase (17β-HSD) such as 17β-HSD type 1, type 2 or type 3 enzyme.

3 Claims, No Drawings

OTHER PUBLICATIONS

M.V. Kapustina et al, "Synthesis and Biological Activity of Derivatives of 4,8-Dioxo-3,4,5,6,7,8-Hexahydrobenzothieno[2,3-d]Pyrimidine", 1992, pp. 73-75, Plenum Publishing Corporation.

M.V. Kapustina et al., "Synthesis and Antitubercular Activity of Benzothieno[2,3-d]Pyrimidines", 1992, pp. 475-477, Plenum Publishing Corporation.

CAS Reg. No. 333774-42-8, STN Chemcats, AN:2003:2522717; 2003:922742; 2002:1972045: 2001:2456686; 2001:1511653; and 2001:908276, downloaded Feb. 24, 2004.

Chemical Abstract, vol. 138, 73238, CAS Registry No. 481726-85-6, downloaded Feb. 24, 2004.

Chemical Abstract. vol. 137, 28319, CAS Registry No. 300815-12-7, downloaded Feb. 24, 2004.

Chemical Abstract, vol. 115, 207945, CAS Registry No. 136918-54-2, downloaded Feb. 24, 2004.

Chemical Abstract, vol. 106. 168814, CAS Registry No. 106858-18-8, downloaded Feb. 24, 2004.

Nahed M. Fathy et al., "Synthesis of Thienopyrimidotriazines, a New Fused Heterocyclic Ring System", Chemical Abstract, No. 1997:778794, XP-002299345.

V.P. Arya, "Synthesis of New Heterocycles.; VI. Syntheses of Certain Novel Condensed Thiophenes", Chemical Abstract, No. 1973:124381, XP-002299346.

M.A. El-Sherbeny et al., "Synthesis, Antimicrobial and Antiviral Evaluation of Certain Thienopyrimidine Derivatives", Chemical Abstract No. 1995:656629, XP-002299347, 1995.

Maria Santagati et al., "Synthesis of Aminothienopyrimidine and Thienotriazolopyrimidine Derivatives as Potential Anticonvulsant Agents", Chemical Abstract, No. 1996:96344, XP-002299348, 1996.

V.P. Arya, "Synthesis of New Heterocycles: Part VI—Synthesis of Certain Novel Condensed Thiophenes" Indian Journal of Chemistry, Dec. 1972, pp. 1141-1150, vol. 10.

M.A. El-Sherbeny et al., "Synthesis, Antimicrobial and Antiviral Evaluation of Certain Thienopyrimidine Derivatives" European Journal of Medicine, 1945, pp. 445-449, vol. 30, Elsevier, Paris.

Nahed M. Fathy et al., "Synthesis of Thienopyrimidotriazines, a New Fused Heterocyclic Ring System", Egypt Journal of Chemistry, 1997, pp. 117-128, vol. 40, No. 20.

Maria Santagati et al., "Synthesis of Aminothienopyrimidine and Thienotriazolopyrimidine Derivatives as Potential Anticonvulsant Agents" Pharmazie, 1996, pp. 7-11, 51, 1.

Khaled Zeitoun et al., Deficient 17β-Hydroxysteroid Dehydrogenase Type 2 Expression in Endometriosis: Failure to Metabolize 17β-Estradiol * Journal of Clinical Endocrinology and Metabolism, vol. 83, No. 12, 1998, Downloaded from jcem.endojournals.org). *Please note: this publication already submitted with Amendment filed on Dec. 19, 2007 Appendix A.*

G.S. Chetrite et al., "The selective estrogen enzyme modulator (SEEM) in breast cancer", Journal of Steroid Biochemistry & Molecular Biology 76, 2001, pp. 95-104, Elsevier Science Ltd.

H. John Smith et al., "Inhibitors of steroidogenesis as agents for the treatment of hormone-dependent cancers", 2001, pp. 789-824, Ashley Publications Ltd. ISSN 1354-3776.

K. Zeitoun et al., "Armoatase: a key molecule in the pathophysiology of endometriosis and a therapeutic target", Fertility and Sterility, vol. 72, No. 6, Dec. 1999, pp. 961-969, Elsevier Science Inc.

S.E. Bulun et al., "Estrogen biosynthesis in endometriosis: molecular basis and clinical relevance", Journal of Molecular Endocrinology, 2000, vol. 25, pp. 35-42, 2000 Society for Endrocrinology.

* cited by examiner

TETRACYCLIC THIOPHENEPYRIMIDINONE COMPOUNDS AS INHIBITORS OF 17β HYDROXYSTEROID DEHYDROGENASE COMPOUNDS

CROSS REFERENCE TO RELATED APPLICATION

This application claims priority from U.S. provisional patent application No. 60/477,017, filed Jun. 10, 2003.

FIELD OF THE INVENTION

The present invention relates to novel thiophenepyrimidinone derivatives which represent inhibitory compounds of the 17β-hydroxysteroid dehydrogenase enzymes, preferably of the 17β-hydroxysteroid dehydrogenase type 1 (17β-HSD1), type 2 (17β-HSD2) or type 3 (17β-HSD3) enzyme, to their salts, to pharmaceutical preparations containing these compounds and to processes for the preparation of these compounds. Furthermore, the invention concerns the therapeutic use of said thiophenepyrimidinone derivatives, particularly their use in the treatment or prevention of steroid hormone dependent diseases or disorders, such as steroid hormone dependent diseases or disorders requiring the inhibition of 17β-hydroxysteroid dehydrogenase enzymes, in particular 17β-HSD type I enzymes, and/or requiring the modulation of the endogenous 17β-estradiol and/or testosterone concentration.

BACKGROUND OF THE INVENTION

The publications and other materials used herein to illuminate the background of the invention, and in particular, cases to provide additional details respecting the practice, are incorporated by reference.

Mammalian 17β-hydroxysteroid dehydrogenases (17β-HSDs) are NAD(H) or NADP(H) dependent enzymes which catalyze—besides other reactions—the final steps in male and female sex hormone biosynthesis. These enzymes convert inactive 17-keto-steroids into their active 17β-hydroxy-forms or catalyze the oxidation of the 17β-hydroxy-forms into the 17-keto-steroids. Because both estrogens and androgens have the highest affinity for their receptors in the 17β-hydroxy form, 17β-HSD enzymes play an essential role in the tissue-selective regulation of the activity of sex steroid hormones.

At present, 10 human members of the 17β-HSD enzyme family have been described (types 1-5, 7, 8, 10, 11 and 12). The human 17β-HSD family members share less than 30% similarity in their primary structure. The 17β-HSDs are expressed in distinct, though in some cases, overlapping patterns. The different types of 17β-HSDs also differ in their substrate and cofactor specificities. In intact cells in culture, the 17β-HSDs catalyze the reaction in a unidirectional way: types 1, 3, 5 and 7 use NADP(H) as a cofactor and catalyze the reductive reaction (activation), while types 2, 4, 8 and 10 catalyze the oxidative reaction (inactivation) using NAD(H) as a cofactor. [see e.g. Labrie et al. (2000) Trends Endocrinol Metab., 11:421-7].

Due to their essential role in the tissue-selective regulation of the activity of sex steroid hormones 17β-HSDs can be involved in the occurrence and development of estrogen-sensitive pathologies (f. ex. breast, ovarian, uterine and endometrium cancers etc.) and androgen-sensitive pathologies (f. ex. prostate cancer, benign prostatic hyperplasia, acne, hirsutism, etc). Furthermore, many types of 17β-HSD have been shown to be involved in the pathogenesis of particular human disorders. For example, 17β-HSD3 is known to be involved in the development of pseudohermaphroditism, the 17β-HSD8 plays a role in polycystic kidney disease and the 17β-HSD4 is related to the occurrence of bifunctional enzyme deficiency. Therefore treatment of sex steroid-sensitive diseases by administration of specific inhibitors of the 17β-HSDs enzymes have been suggested, optionally in combination with potent and specific antiestrogens and antiandrogens [Labrie F et al. (1997) Steroids, 62:148-58].

Due to the fact that each type of 17β-HSD has a selective substrate affinity, directional (reductive or oxidative) activity in intact cells, and a particular tissue distribution, the selectivity of drug action could be achieved by targeting a particular 17β-HSD isozyme. By individual modulation of the particular 17β-HSDs it is possible to influence or even control the local and paracrine concentration of estrogens and androgens in different target tissues.

The best characterized member of the 17β-HSD family is the type 1 17β-HSD [EC 1.1.1.62]. This enzyme could be crystallized in different states of functionality (e.g. with and without ligand and/or co-factor). The 17β-HSD1 catalyzes in vitro the reduction as well as the oxidation between estrone (E1) and estradiol (E2). However, under physiological in vivo conditions the enzyme only catalyzes the reductive reaction from the estrone (E1) to the estradiol (E2). The 17β-HSD1 was found to be expressed in a variety of hormone-dependent tissues, e.g. placenta, mammary gland tissue or uterus and endometrium tissue, respectively. Estradiol itself is, especially in comparison to the significantly less active estrone, a very potent hormone, which regulates the expression of a variety of genes by binding to the nuclear estrogen receptor and plays an essential role in the proliferation and differentiation of the target cell. Physiological as well as pathological cell proliferations can be estradiol dependent. Especially many breast cancer cells are stimulated by a locally raised estradiol concentration. Furthermore, the occurrence or course of benign pathologies such as endometriosis, uterine leiomyomas (fibroids or myomas), adenomyosis, menorrhagia, metrorrhagia and dysmenorrhea is dependent from the existence of significantly high estradiol levels.

Endometriosis is a well-known gynecological disorder that affects 10 to 15% of women in the reproductive age. It is a benign disease defined as the presence of viable endometrial gland and stroma cells outside the uterine cavity. It is most frequently found in the pelvic area. In women developing endometriosis, the endometrial cells entering the peritoneal cavity by retro-grade menstruation (the most likely mechanism) have the capacity to adhere to and invade the peritoneal lining, and are then able to implant and grow. The implants respond to steroid hormones of the menstrual cycle in a similar way as the endometrium in the uterus. The infiltrating lesions and the blood from these lesions which are unable to leave the body cause inflammation of the surrounding tissue. The most common symptoms of endometriosis are dysmenorrhoea, dyspareunia and (chronic) abdominal pain. The occurrence of these symptoms is not related to the extent of the lesions. Some women with severe endometriosis are asymptomatic, while women with mild endometriosis may have severe pain. Endometriosis is found in up to 50% of the women with infertility. However, currently no causal relation has been proven between mild endometriosis and infertility. Moderate to severe endometriosis can cause tubal damage and adhesions leading to infertility. The aims of treatment of endometriosis are pain relief, resolution of the endometriotic tissue and restoration of fertility (if desired). The two common treatments are surgery or anti-inflammatory and/or hormonal therapy or a combination thereof.

Uterine leiomyomas (fibroids or myomas), benign clonal tumours, arise from smooth muscle cells of the human uterus. They are clinically apparent in up to 25% of women and are the single, most common indication for hysterectomy. They cause significant morbidity, including prolonged and heavy menstrual bleeding, pelvic pressure and pain, urinary problems, and, in rare cases, reproductive dysfunction. The pathophysiology of myomas is not well understood. Myomas are found submucosally (beneath the endometrium), intramurally (within the myometrium) and subserosally (projecting out of the serosal compartment of the uterus), but mostly are mixed forms of these 3 different types. The presence of estrogen receptors in leiomyoma cells has been studied by Tamaya et al. [Tamaya et al. (1985) Acta Obstet Gynecol Scand., 64:307-9]. They have shown that the ratios of estrogen receptor compared to progesterone and androgen receptor levels were higher in leiomyomas than in the corresponding normal myometrium. Surgery has long been the main treatment for myomas. Furthermore, medical therapies that have been proposed to treat myomas include administration of a variety of steroids such as the androgenic steroids danazol or gestrinone, GnRH agonists and progestogens, whereby the administration is often associated a variety of serious side-effects.

Everything that has been said above in relation to the treatment of uterine leiomyomas and endometriosis equally applies to other benign gynaecological disorders, notably adenomyosis, functional menorrhagia and metrorrhagia. These benign gynaecological disorders are all estrogen sensitive and are treated in a comparable way as described herein before in relation to uterine leiomyomas and endometriosis. The available pharmaceutical treatments, however, suffer from the same major drawbacks, i.e. they have to be discontinued once the side-effects become more serious than the symptoms to be treated and symptoms reappear after discontinuation of the therapy.

Since the aforementioned malign and benign pathologies are all 17β-estradiol dependent, a reduction of the endogenous 17β-estradiol concentration in the respective tissue will result in an impaired or reduced proliferation of 17β-estradiol cells in said tissues. Therefore, it may be concluded that selective inhibitors of the 17β-HSD1 enzyme are well suited for their use to impair endogenous productions of estrogens, in particular of 17β-estradiol, in myomas, endometriotic, adenomyotic and endometrial tissue. The application of a compound acting as selective inhibitor on the 17β-HSD1 which preferentially catalyzes the reductive reaction will result in a lowered intracellular estradiol-concentration since the reductive conversion of the estrone into the active estradiol is reduced or suppressed. Therefore, reversible or even irreversible inhibitors of the 17β-HSD1 may play a significant role in the prophylaxis and/or treatment of steroid-hormone, in particular 17β-estradiol, dependent disorders or diseases. Furthermore, the reversible or even irreversible inhibitors of the 17β-HSD1 should have no or only pure antagonistic binding activities to the estradiol receptor, in particular to the estrogen receptor α subtype, since agonistic binding of the estrogen receptor would lead to activation and therefore—by regulation of a variety of genes—to the proliferation and differentiation of the target cell. In contrast, antagonists of the estrogen receptor, so called anti-estrogens, bind competitively to the specific receptor protein thus preventing access of endogenous estrogens to their specific binding site. At present it is described in the literature that several malignant disease as breast cancer, prostate carcinoma, ovarian cancer, uterine cancer, endometrial cancer and endometrial hyperplasia may be treated by the administration of a selective 17β-HSD1 inhibitor. Furthermore, a selective 17β-HSD1 inhibitor may be useful for the prevention of the aforementioned hormone-dependent cancers, especially breast cancer.

Several reversible or irreversible inhibitors of the 17β-HSD1 enzyme of steroidal and even non-steroidal origin are already known from the literature. The characteristics of these inhibitory molecules, which mainly have a substrate or cofactor-like core structure, have been reported in the literature [reviewed in: Poirier D. (2003) Curr Med Chem. 10:453-77].

A further well characterized member of the 17β-HSD family is the 17β-HSD type 3 enzyme (17β-HSD3). The 17β-HSD3 has a distinct feature compared to other 17HSDs: it is found to be expressed almost exclusively the testis, whereas the other isoenzymes are expressed more widely in several tissues. 17β-HSD3 has a crucial role in androgen biosynthesis. It converts 4-androstene-3,17-one (A) to testosterone (T). The biological significance of the 17β-HSD3 is of undeniable physiological importance. Mutations in the gene for 17β-HSD3 have found to lead to decreased T formation in the fetal testis and consequently to a human intersex disorder termed male pseudohermaphroditism [Geissler W M et al. (1994) Nat Genet., 7:34-9].

With regard to the indication prostate cancer, the primary cancer cells mostly retain their responsiveness to androgens in their regulation of proliferation, differentiation, and programmed cell death for some period. At present, androgen deprivation is the only effective systemic hormonal therapy available for prostate cancer. The development of selective inhibitors against 17β-HSD3 is a new therapeutic approach for the treatment of androgen dependent disease [Labrie et al. (2000) Trends Endocrinol Metab., 11:421-7]. Furthermore, Oefelein et al. reported that the depot GnRH analogue fails, in nearly 20% of cases, to achieve castrate levels of T in men [Oefelein MG & Cornum R (2000) J Urol.; 164:726-9]. In order to improve the response rate to endocrine therapy for men with prostate cancer it may be important to selectively inhibit testicular 17β-HSD3 activity. Besides prostate cancer, many other androgen-sensitive diseases, i.e. diseases whose onset or progress is aided by androgenic activity, may be treated by selectively inhibiting 17β-HSD3 activity. These diseases include but are not limited to benign prostatic hyperplasia, prostatitis, acne, seborrhea, hirsutism, androgenic alopecia, precocious puberty, adrenal hyperplasia, and polycystic ovarian syndrome. Furthermore, considering the fact that 17β-HSD3 is found mainly in the testis, the development of potent inhibitors could be of interest for blocking spermatogenesis and as an anti-fertility agent for males.

Several reversible or irreversible inhibitors of the 17β-HSD3 enzymes of steroidal and even non-steroidal origin are already known from the literature. The characteristics of these inhibitory molecules have been reported in the literature [reviewed in: Poirier D. (2003) Curr Med Chem. 10:453-77]. For example, U.S. Pat. No. 6,541,463 discloses androsterone derived inhibitors for 17β-HSD3. These derivatives have been synthesised by parallel solid- and liquid-phase chemistry and some of these compounds showed 2 to 18-fold higher inhibition activity than that of the natural substrate of the enzyme, A-dione, used itself as a inhibitor. Furthermore, the international patent application WO 01/42181 discloses benzyl-tetralins, the chemical structure of which is related to that of the phytoestrogen biochanin, as 17β-HSD3 inhibitors. Furthermore, international patent applications WO 98/32724, WO 98/30556 and WO 99/12540 disclose tetralone, benzopyrane and benzofuranone derivatives, which have a 17β-HSD inhibitory activity, for the treatment of hormone sensitive diseases.

Microsomal 17β-hydroxysteroid dehydrogenase of human endometrium and placenta (designated 17β-HSD type 2 or 17β-HSD2) was cloned by expression cloning, and found to be equally active using androgens and estrogens as substrates for oxidation [Andersson S. (1995) J. Steroid Biochem. Molec. Biol., 55:533-534]. The recombinant 17β-HSD2 converts the highly active 17β-hydroxysteroids such as estradiol (E2), testosterone (T), and dehydrotestosterone (DHT) to their inactive keto forms. In addition, the 17β-HSD2 can, to a lesser extent, also convert 20β-hydroxyprogesterone (20βP) to progesterone (P). The broad tissue distribution together with the predominant oxidative activity of 17β-HSD2 suggest that the enzyme may play an essential role in the inactivation of highly active 17β-hydroxysteroids, resulting in diminished sex hormone action in target tissues. Dong and colleagues showed significant 17β-HSD2 activity in cultured human osteoblasts and osteoblast-like osteosarcoma cells MG63 and TE85, but not in SaOS-2 [Dong Y et al. (1998) J. Bone Min. Res., 13:1539-1546]. The potential for interconversion of E1 to E2, T to A, and DHT to A by bone cells could therefore represent important mechanism for the local regulation of intracellular ligand supply for the estrogen and androgen receptors in the osteoblasts and other steroid sensitive cells. This modulation of steroid levels may be employed for a wide variety of indications, including the following: for the prevention and treatment of osteoporosis, for the treatment of ovarian cancer, for the treatment of breast cancer, for the treatment of endometrial cancer, for the treatment of endometriosis, for the treatment of prostate cancer and/or for the treatment of androgen-dependent hair-loss.

Several reversible or irreversible inhibitors of the 17β-HSD2 enzymes of steroidal and even non-steroidal origin are already known from the literature. The characteristics of these inhibitory molecules have been reported in the literature [reviewed in: Poirier D. (2003) Curr Med Chem. 10:453-77]. In addition, the international patent application WO 02/26706 discloses 17β-HSD2 inhibitors of non-steroidal origin.

Some thienopyrimidinones derivatives that are described as being useful in therapy have already been disclosed in the literature: The German patent application DE 2411273 (Schering AG) discloses compounds having anti-inflammatory activity. Manhas et al describe the synthesis and antiinflammatory activity of some substituted thienopyrimidinones [Manhas M S et al. (1972) J Med Chem. 15(1):106-7]. Kapustina et al. describe the synthesis and antibacterial and chemotherapeutic or antitubecular activity of some substituted thienopyrimidones [Kapustina M V et al. (1992) Khimiko-Farmatsevticheskii Zhurnal 26(1):56-7; and Kapustina M V et al (1991) Khimiko-Farmatsevticheskii Zhurnal 25(7): 38-9].

Furthermore, several other Thienopyrimidinones derivatives have been described but were not related to any medical use so far. For example, the compounds 1,2,7,8,9,10,11,13-octahydro-13-oxo-4-(phenylthio)-[1]benzothieno[2',3':4,5]pyrimido[1,2-a]azepine-3-carboxaldehyde (CAS reg. no. 333774-42-8) and 1,2,7,8,9,10,11,13-octahydro-13-oxo-4-(chloro)-[1]benzothieno-[2',3':4,5]pyrimido[1,2-a]azepine-3-carboxaldehyde (CAS reg. no 299962-60-0) are commercially available. Further substituted thienopyrimidones have already been disclosed, e.g.:

1,2,7,8,9,10,11,13-octahydro-4-hydroxy-[1]benzothieno[2', 3':4,5]pyrimido[1,2-a]azepin-13(7H)-one (CA reg. no. 333774-26-8);

2,3,8,9,10,11-hexahydro-[1]benzothieno[2',3':4,5]pyrimido [1,2-a]azepine-4,13(1H,7H)-dione (CA reg. no. 141581-80-8);

2,3,8,9-Tetrahydro[1]benzothieno[2,3-d]pyrrolo[1,2-a]pyrimidine-6,10(1H,7H)-dione (CA reg. no. 141581-81-9), 8,9,10,11-tetrahydro-4-hydroxy-[1]benzothieno[2',3':4,5] pyrimido[1,2-a]azepin-13(7H)-one (CA reg. no. 333780-19-1);

3-Butyl-2,7-dimethyl-4b,5,6,7,8,8a-hexahydro-3H-benzo[4, 5]thieno[2,3-d]pyrimidin-4-one (CA reg. no. 39625-80-4);

1,2,3,4,5,8,9,10,11,12-Decahydro-14H-cyclohepta[4',5] thieno[2',3':4,5]pyrimido-[1,2-a]azepin-14-one-4-oxime (CA reg. no. 299962-59-7);

1,2,3,4,5,8,9,10,11,12-Decahydro-14H-cyclohepta[4',5] thieno[2',3':4,5]pyrimido-[1,2-a]azepin-14-one-3-oxime (CA reg. no. 296798-31-7);

1,2,3,4,7,9,10,12-Octahydro-12-oxo-8H-[1]benzothieno[2, 3-d]pyrido[1,2-a]pyrimidine-7-carboxylic acid ethyl ester (CA reg no. 329059-69-0);

1,2,3,4-Tetrahydro-12H-[1]benzothieno[2,3-d]pyrido[1,2-a] pyrimidin-12-one (CA Reg. No. 60943-07-9), and 3-Methyl-2,3,4,7,8,9,10,11-octahydro-[1]benzothieno[2',3': 4,5]pyrimido-[1,2-a]azepin-13(1H)-one (CA Reg. No. 677320-14-8)

However, according to the inventors' knowledge none of the already known compounds described above has been described as useful in the treatment and/or prevention of a steroid hormone dependent disease or disorder, particularly a steroid hormone dependent disease or disorder requiring the inhibition of the 17β-hydroxysteroid dehydrogenase (17HSD) type 1, type 2 or type 3 enzyme.

There is a need for the development of compounds that are selectively inhibiting the 17β-HSD1, 17β-HSD3 and/or 17β-HSD2 enzyme, while desirably failing to inhibit substantially other members of the 17β-HSD protein family, or other catalysts of sex steroid degradation or activation. In particular, it is an aim of the present invention to develop selective inhibitors of the 17β-HSD1 enzyme, whereby in addition the compounds have no or only pure antagonistic binding affinities to the estrogen receptor (both subtypes α and β).

SUMMARY OF THE INVENTION

Therefore, it is an object of the present invention to provide novel inhibitors of the 17β-HSD1 and 17β-HSD2 enzyme, which have valuable pharmacological properties and which are suited for the treatment of estrogen dependent diseases and disorders. It is a further object of the present invention to develop novel inhibitors of the 17β-HSD3 enzyme, which have valuable pharmacological properties and which are suited for the treatment of androgen dependent diseases and disorders.

It has now been found that the thiophenepyrimidinone derivatives of the present invention would be valuable in therapy, especially in the treatment or prevention of steroid hormone dependent diseases or disorders, such as steroid hormone dependent diseases or disorders requiring the inhibition of 17β-hydroxysteroid dehydrogenase (HSD) enzymes. In particular, compounds of formula (I) represent potent inhibitors of the 17β-HSD1, 17β-HSD3 and/or 17β-HSD2 enzyme and possess valuable pharmacological properties for the treatment and/or prophylaxis of malignant steroid dependent diseases or disorders such as breast cancer, prostate carcinoma, ovarian cancer, uterine cancer, endometrial cancer and endometrial hyperplasia, but also for the treatment and/or prophylaxis of benign steroid dependent diseases or disorders such as endometriosis, uterine fibroids, uterine leiomyoma, adenomyosis, dysmenorrhea, menorrhagia, metrorrhagia, prostadynia, benign prostatic hyperplasia, prostatitis, acne, seborrhea, hirsutism, androgenic alopecia, precocious puberty, adrenal hyperplasia, polycystic ovarian syndrome, or urinary dysfunction. Further estrogen-dependent diseases which may be treated and/or prevented with an effective amount of a compound of the invention are multiple sclerosis, rheumatoid arthritis, Alzheimer's disease, colon cancer, tissue wounds, skin wrinkles and cataracts. Furthermore, compounds of formula (I) may be useful for the prevention and treatment of osteoporosis, and for blocking spermatogenesis and as an anti-fertility agent for males.

Accordingly, the present invention relates to the use of a compound having the structural formula (I)

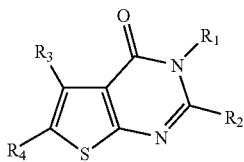

(I)

wherein $R_1$ and $R_2$ represent the same or different alkyl, or one is alkyl and the other is H, or $R_1$ and $R_2$ form together with their binding sites a cyclic 5-, 6-, 7- or 8-membered ring system, which is saturated or contains one or more double bonds between the ring atoms, and which ring optionally contains up to two heteroatoms in addition to the nitrogen atom where $R_1$ is attached, the number of N atoms being 0-2 and the number of O or S atoms each being 0-1, wherein said ring is optionally substituted with up to three substituents independently selected from the group consisting of alkyl, substituted alkyl, aryl, or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido;

$R_3$ and $R_4$ form together with their binding sites a cyclic 5-, 6-, 7- or 8-membered hydrocarbon ringsystem, which is saturated or contains one or more double bonds between the carbon atoms, and wherein said ring is optionally substituted with up to three substituents independently selected from the group consisting of alkyl, substituted alkyl, aryl or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido;

provided that said compound is not 1,2,7,8,9,10,11,13-octahydro-13-oxo-4-(phenylthio)-[1]benzothieno[2',3':4,5]pyrimido[1,2-a]azepine-3-carboxaldehyde;

for the manufacture of a medicament for the treatment and/or prevention of a steroid hormone dependent disease or disorder, preferably for a steroid hormone dependent disease or disorder requiring the inhibition of a 17β-hydroxysteroid dehydrogenase (17β-HSD) enzyme, most preferably requiring the inhibition of the 17β-HSD type 1, 17β-HSD type 2 or 17β-HSD type 3 enzyme.

According to another aspect, the invention concerns a compound of formula (II)

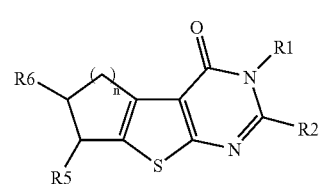

(II)

wherein $R_1$ and $R_2$ represent the same or different $C_1$-$C_8$-alkyl, or one is $C_1$-$C_8$-alkyl and the other is H, or $R_1$ and $R_2$ form together with their binding sites a cyclic 5-, 6-, 7- or 8-membered ring system, which is saturated or contains one or more double bonds between the ring atoms, and which ring optionally contains up to two N-atoms in addition to the nitrogen atom where $R_1$ is attached, wherein said ring is optionally substituted with up to two substituents independently selected from the group consisting of alkyl, substituted alkyl, aryl, or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido;

the hydrocarbon chain —C(R5)—C(R6)—(CH)$_n$— of the ring-system adjacent to the thiophen-ring is saturated or contains one or more double bonds between the carbon atoms;

n is an integer from 1 to 4, and

R5 and R6 are individually selected from the group consisting of hydrogen, alkyl, substituted alkyl, aryl or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido.

under the proviso that in case n represents 1, 2 or 3, and R1 and R2 independently are selected from hydrogen or $C_1$-$C_4$ alkyl or together form an unsubstituted alkylen group of 3-5 methylen groups or a iminoalkylen group of 2-4 methylen groups in the alkylen group, optionally substituted at the N-atom, then at least (i) R5 or R6 has to be different from hydrogen, $C_1$-$C_4$ alkyl or alkylcarboxyl, or (ii) the hydrocarbon chain —C(R5)—C(R6)—(CH)$_n$— of the ring-system adjacent to the thiophen-ring has to be unsaturated or aromatic;

in case n represents 2 and R1-R2 form an unsubstituted alkylen group of 3-5 methylen groups, then R6 has to be different from bromo, dibromo or phenylthio, if R5 represents a hydroxyl or oxo group; or in case n represents 2 and R1-R2 form an unsubstituted pentamethylen group, then R5 has to be different from phenylthio, if R6 represents carbonyl, for use in therapy.

According to a third aspect, the invention concerns a novel compound of formula (II)

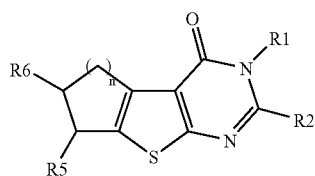

(II)

wherein

R$_1$ and R$_2$ represent the same or different C$_1$-C$_8$-alkyl, or one is C$_1$-C$_8$-alkyl and the other is H, or R$_1$ and R$_2$ form together with their binding sites a cyclic 5-, 6-, 7- or 8-membered ring system, which is saturated or contains one or more double bonds between the ring atoms, and which ring optionally contains up to two N-atoms in addition to the nitrogen atom where R1 is attached, wherein said ring is optionally substituted with up to two substituents independently selected from the group consisting of alkyl, substituted alkyl, aryl, or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido;

the hydrocarbon chain —C(R5)—C(R6)—(CH)$_n$— of the ring-system adjacent to the thiophen-ring is saturated or contains one or more double bonds between the carbon atoms;

n is an integer from 1 to 4, and

R5 and R6 are individually selected from the group consisting of hydrogen, alkyl, substituted alkyl, aryl or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido.

under the proviso that in case n represents 1, 2 or 3, and R1 and R2 are independently selected from hydrogen or C$_1$-C$_4$ alkyl or form together an unsubstituted alkylen group of 3-5 methylen groups or a iminoalkylen group with 2-4 methylen groups in the alkylen group, optionally substituted at the N-atom, then at least (i) R5 or R6 has to be different from hydrogen, C$_1$-C$_4$ alkyl, alkylcarboxyl, or =N—OH, or (ii) the hydrocarbon chain —C(R5)—C(R6)—(CH)$_n$— of the ring-system adjacent to the thiophen-ring has to be aromatic, and at least R5 or R6 has to be different from hydrogen;

in case n represents 2 and R1-R2 form an unsubstituted alkylen group of 3 or 5 methylen groups, then R6 has to be different from hydrogen, bromo, dibromo or phenylthio, if R5 represents a hydroxyl or oxo group;

in case n represents 2 and R1-R2 form an unsubstituted pentamethylen group, then R5 has to be different from phenylthio or chloro, if R6 represents carbonyl;

in case n represents 2, the hydrocarbon chain —C(R5)—C(R6)—(CH)$_n$— of the ring-system adjacent the thiophene-ring is saturated and R1-R2 together with their binding sites form an unsubstituted pyridine-ring, then at least one of R5 or R6 has to be different from hydrogen; or in case —C(R5)—C(R6)—(CH)$_n$— represents an unsubstituted tetramethylen group, R1-R2 have to be different from a tetramethylen group substituted with a carboxylethyl-ester group.

According to a fourth aspect, the invention concerns a pharmaceutical composition comprising as active agent a compound of formula (II) as defined herein, for which no use in therapy earlier has been disclosed, and at least a pharmaceutically acceptable carrier.

According to a fifth aspect, the invention concerns the use of a compound of formula (I), more preferably of formula (II), as defined herein, for the treatment or prevention of a steroid hormone dependent disease or disorder. Preferably, the steroid hormone dependent disease or disorder is a disease or disorder requiring the inhibition of a 17β-hydroxysteroid dehydrogenase enzyme, preferably of the 17β-HSD type 1, 17β-HSD type 2 or 17β-HSD type 3.

According to a sixth aspect the invention concerns a method for the preparation of the novel compounds of formula (I) wherein a) a compound of formula 2

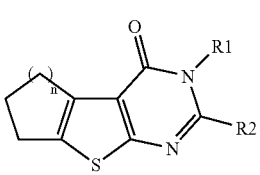

(2)

or a ring-substituted or ring-modified analogue thereof is oxidized, preferably by subjecting to PCC and celite, to give an oxo-substituted compound of formula 3 or an analogue thereof,

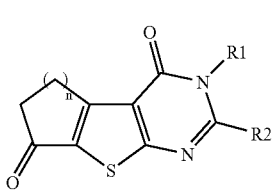

(3)

b) the oxo-substituted compound obtained in step a) is optionally further subjected to Vilsmeier reaction, preferably by POCl$_3$-DMF, to give a carbonylsubstituted compound of formula 4 or an analogue thereof,

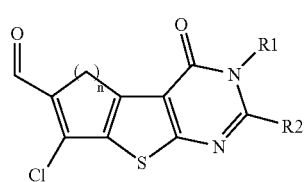

(4)

c) the chlorosubstituent in the carbonylsubstituted compound obtained in step b) is optionally further replaced by an alkylthio or an arylthio group by subjecting to an appropriate thiol in the presence of a base to give an arylthio- or alkylthiosubstituted compound of formula 5 or an analogue thereof,

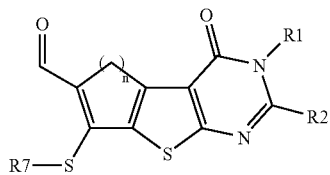

(5)

d) the arylthio- or alkylthiosubstituted compound obtained in step c) is optionally further
   i) reduced to a compound of formula 6,

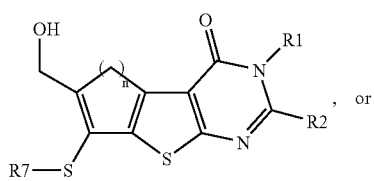

(6)

, or ii) reacted with NH2OH to give a compound of formula 7,

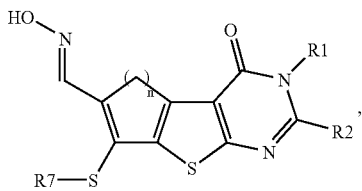

(7)

or e) the compound obtained in step b) is optionally further
   i) reduced so as to replace the carbonyl group with hydroxyalkyl, or
   ii) subjected to an appropriate thiol in the presence of a base and acetone, so as to replace the chloro substituent by a thiol group and to replace the carbonyl group with an oxosubstituted alkenyl.

or f) the compound obtained in step a) is optionally further subjected to DMF acetal so as to introduce a dimethylaminomethylene substituent in the ring next to the oxo substituent.

DETAILED DESCRIPTION

Definitions:

The following terms are used to describe various constituents of the chemical composition useful in this invention. The terms are defined as follows:

As used herein, the terms "comprising" and "including" are used herein in their open, non-limiting sense.

The word "compound" shall here be understood to cover any and all isomers (e.g., enantiomers, stereoisomers, diastereomers, rotomers, and tautomers), racemates or any mixture of isomers, prodrugs, and any pharmaceutically acceptable salt of said compound.

Where the plural form is used for compounds, salts, and the like, this is taken to mean also a single compound, salt, or the like.

The term "substituted" means that the specified group or moiety bears one or more substituents. Where any group may carry multiple substituents and a variety of possible substituents is provided, the substituents are independently selected and need not be the same. The term "unsubstituted" means that the specified group bears no substituents. The term "optionally substituted" means that the specified group is unsubstituted or substituted by one or more substituents.

Any asymmetric carbon atoms may be present in the (R)—, (S)— or (R,S)-configuration, preferably in the (R)— or (S)-configuration, whichever is most active. Substituents at a double bond or a ring may be present in cis-(.=Z—) or trans (=E—) form.

The compounds of the present invention may contain asymmetric centers on the molecule, depending upon the nature of the various substituents. In certain instances, asymmetry may also be present due to restricted rotation about the central bond adjoining the two aromatic rings of the specified compounds. It is intended that all isomers (including enantiomers and diastereomers), either by nature of asymmetric centers or by restricted rotation as described above, as separated, pure or partially purified isomers or racemic mixtures thereof, be included within the ambit of the instant invention.

The term "halogen" refers to fluorine (F, Fluoro-), bromine (Br, Bromo-), chlorine (Cl, Chloro), and iodine (J, Iodo-) atoms. Preferred in the context of the present invention are Br, Cl and F.

The terms "dihalogen", "trihalogen" and "perhalogen" refer to two, three and four substituents, respectively, each individually selected from the group consisting of fluorine, bromine, chlorine, and iodine atoms.

The term "hydroxyl" refers to the group —OH

The term "oxo" refers to the group =O

The term "thio" refers to the group =S

The term "thiol" refers to the group —SH

The term "sulfonyl" refers to the group —S(O)$_{1-2}$—

For the purpose of the present invention, the carbon content of various hydrocarbon containing moieties is indicated by a prefix designating the minimum and maximum number of carbon atoms in the moiety, i.e., the prefix $C_i$-$C_j$ defines the number of carbon atoms present from the integer "i" to the integer "j" inclusive. Thus $C_1$-$C_4$-alkyl refers to alkyl of 1-4 carbon atoms, inclusive, or methyl, ethyl, propyl, butyl and isomeric forms thereof.

The term "alkyl" stands for a hydrocarbon radical which may be linear, cyclic or branched, with single or multiple branching, whereby the alkyl group comprises 1 to 12 carbon atoms. In one embodiment, the term "alkyl" stands for a linear or branched (with single or multiple branching) alkyl chain of 1 to 8 carbon atoms, exemplified by the term ($C_1$-$C_8$)alkyl, more preferably of 1 to 4 carbon atoms exemplified by the term ($C_1$-$C_4$)alkyl. The term ($C_1$-$C_8$)alkyl is further exemplified by such groups as methyl; ethyl; n-propyl; isopropyl; n-butyl; sec-butyl; isobutyl; tert-butyl; n-pentyl; isopentyl; neopentyl; tert-pentyl; 2- or 3-methylpentyl; n-hexyl; isohexyl, and the like. The alkyl group may be partially unsaturated, forming such groups as, for example, methylenyl, ethenyl, ethylenyl, propenyl (allyl), methyl-propenyl, butenyl, pentenyl, pentinyl, hexenyl, octadienyl, and the like. The term "alkyl" further comprises cycloalkyl groups, preferably cyclo($C_3$-$C_8$)alkyl which refers to cyclopropyl, cyclobutyl, cyclopentyl, cyclohexyl, cycloheptyl, cyclooctyl and isomeric forms thereof such as methylcyclopropyl; 2- or 3-methylcyclobutyl; 2-, or 3-methylcyclopentyl, and the like. The cycloalkyl group may also be partly unsaturated, forming such groups as, for example, cyclohexenyl, cyclopentenyl, cyclooctadienyl, and the like. Furthermore, the term "alkyl" comprises a cycloalkyl-alkyl group comprising 4 to 12 carbon atoms, preferably "cyclo($C_3$-$C_8$)alkyl-($C_1$-$C_4$)alkyl" which refers to a alkyl group of 1 to 4 carbon atoms as described above substituted with a cyclo($C_3$-$C_8$)alkyl group as described above, forming such groups as for example cyclopropylmethyl, cyclohexylmethyl, cyclopentylethyl or cyclohexenylethyl.

The term "substituted alkyl" refers to alkyl as just described and substituted by up to five, more preferably by up to three, most preferably by one or two substituents independently selected from the group consisting of halogen, hydroxyl, thiol, nitro, nitrile, alkoxy, aryloxy, acyloxy, amino, imino, oxime, amido, acylamino, alkylthio, arylthio, acyl, carboxyl, sulfamoyl, sulfonamide, and alkylsulfonyl, as defined herein. These groups may be attached to any carbon atom of the alkyl moiety. Substituted alkyl is preferably substituted with hydroxyl, $C_1$-$C_4$-alkoxy, $C_1$-$C_8$-alkylthio, arylthio, preferably phenylthio, an alkylacyl group —CO—R", a carboxyl group —(C=O)—OR", an alkylamino group —NR$_{12}$, an alkylimino group =N—R", or an alkyloxime group =N—O—R", wherein R" represents hydrogen or $C_1$-$C_4$-alkyl. Preferably substituted alkyl refers to substituted $C_1$-$C_4$-alkyl, preferably methyl, substituted methylen and substituted $C_2$-$C_4$-alkenyl.

The term "alkoxy" refers to a group —OR, where R may be alkyl, arylalkyl, or substituted arylalkyl as defined herein, wherein the alkyl chain may be optionally further substituted as defined herein. Preferably, the term "alkoxy" refers to —O—($C_1$-$C_4$)alkyl (or ($C_1$-$C_4$)alkoxy), with the ($C_1$-$C_4$) alkyl group as defined above, or to —O—($C_1$-$C_4$)alkyl-phenyl, preferably benzoxy or phenethyloxy, optionally substituted in the aryl group with up to five independently selected substituents, in particular hydroxyl, halogen, ($C_1$-$C_4$)-alkyl, or ($C_1$-$C_4$)-alkoxy; the number of said substituents being up to five for halogen, and up to three for any combination of said other substituents.

The term "aryloxy" refers to a group —OAr, where Ar may be aryl, or substituted aryl, as defined herein. Preferably, Ar represents aryl as defined herein, which is optionally substituted in the aryl group with up to five independently selected substituents, in particular hydroxyl, halogen, ($C_1$-$C_4$)-alkyl, or ($C_1$-$C_4$)-alkoxy; the number of said substituents being up to five for halogen, and up to three for any combination of said other substituents. Preferably, aryloxy refers to phenoxy, optionally substituted as defined above.

The term "acyloxy" refers to a group —O—CO—R, where R may be alkyl, arylalkyl, substituted arylalkyl, aryl, or substituted aryl, as defined herein, wherein the alkyl chain may be optionally further substituted as defined herein.

The term "alkylacyloxy" represents a preferred selection of the term "acyloxy" and refers to the group —O—CO—$C_1$-$C_{12}$-alkyl, preferably to —O—CO—$C_1$-$C_8$-alkyl, and most preferably to —O—CO—$C_1$—$C_4$-alkyl.

The term "arylacyloxy" represents a preferred selection of the term "acyloxy" and refers to the group —O—CO—Ar, wherein Ar represents aryl as defined herein, preferably phenyl, which is optionally substituted in the aryl group with up to five independently selected substituents, in particular hydroxyl, halogen, ($C_1$-$C_4$)-alkyl, or ($C_1$-$C_4$)-alkoxy; the number of said substituents being up to five for halogen, and up to three for any combination of said other substituents The term "acyl" refers to a group —(C=O)—R, where R may be hydrogen, alkyl, aryl or aryl-($C_1$—$C_4$)-alkyl (both optionally substituted in the aryl group with independently selected substituents as defined herein), as defined herein. Preferably, the term "acyl" refers to a group —(C=O)—R', where R' represents hydrogen, ($C_1$-$C_4$)alkyl, phenyl, or phenyl-($C_1$-$C_4$)alkyl, preferably benzyl.

The term "carbonyl" represents a preferred selection of the term "acyl" and refers to the group —CHO.

The term "alkylacyl" represents a preferred selection of the term "acyl" and refers to a group —(C=O)alkyl, preferably —(C=O)—($C_1$-$C_4$)alkyl.

The term "arylacyl" represents a preferred selection of the term "acyl" and refers to the group —CO—Ar, wherein Ar represents aryl as defined herein, preferably phenyl, which is optionally substituted in the aryl group as defined herein.

The term "carboxyl" refers to a group —(C=O)—OR, where R may be hydrogen, alkyl, substituted alkyl, aryl or aryl-($C_1$-$C_4$)-alkyl (both optionally substituted in the aryl group with independently selected substituents as defined herein), as defined herein. Preferably, the term "carboxyl" refers to a group —(C=O)—OR', where R' represents hydrogen, ($C_1$-$C_4$)alkyl, phenyl, or ($C_1$-$C_4$)alkyl-phenyl, preferably benzyl; whereby the phenyl moiety may be optionally substituted with substituents independently selected from the group consisting of hydroxyl, halogen, ($C_1$-$C_4$)alkoxy, and ($C_1$-$C_4$)-alkyl, the number of said substituents being up to five for halogen, and up to three for any combination of said other substituents.

The term "alkylcarboxyl" represents a preferred selection of the term "carboxyl" and refers to a group —(C=O)—OR, where R is hydrogen or $C_1$-$C_4$ alkyl.

The term "thio-carboxyl" refers to a group —(C=O)—SR, where R may be hydrogen, alkyl, substituted alkyl, aryl or aryl-($C_1$-$C_4$)-alkyl (both optionally substituted in the aryl group with independently selected substituents as defined herein), as defined herein. Preferably, the term "thiocarboxyl" refers to a group —(C=S)—OR', where R' represents hydrogen, ($C_1$-$C_4$)alkyl, phenyl, or ($C_1$-$C_4$)alkyl-phenyl, preferably benzyl; whereby the phenyl moiety may be optionally substituted with substituents independently selected from the group consisting of hydroxyl, halogen, ($C_1$-$C_4$)alkoxy, and ($C_1$-$C_4$)-alkyl, the number of said substituents being up to five for halogen, and up to three for any combination of said other substituents.

The terms "alkylthio" ("alkylsulfanyl") and "alkylsulfonyl" refers to a group —SR and —S(O)$_{n=1-2}$—R, respectively, where R may be alkyl, substituted alkyl, arylalkyl, or substituted arylalkyl, as defined herein. Preferably, the term "alkylthio" ("alkylsulfanyl") refers to a group —SR'and the term "alkylsulfonyl" refers to a group —S(O)$_{n=1-2}$—R', respectively, where R' represents ($C_1$-$C_4$)alkyl, or ($C_1$-$C_4$)alkyl-phenyl, preferably benzyl; optionally substituted in the alkyl chain with up to three substituents as defined herein, preferably hydroxyl, ($C_1$-$C_4$)-alkoxy or halogen.

The term "arylthio" ("arylsulfanyl") and "arylsulfonyl" refers to a group —S—Ar and —S(O)$_{n=1-2}$—Ar, respectively, where Ar represents aryl, or substituted aryl, as defined herein. Preferably Ar represents aryl, which is optionally substituted in the aryl group with independently selected substituents as defined herein, in particular hydroxyl, halogen, ($C_1$-$C_4$)-alkyl, or ($C_1$-$C_4$)-alkoxy, the number of said substituents being up to five for halogen, and up to three for any combination of said other substituents. Preferably, arylthio refers to phenylsulfanyl, optionally substituted as defined above.

The term "amino" refers to the group —NRR', where R and R' may independently be hydrogen, alkyl (optionally substituted in the alkyl chain with up to five independently selected substituents as defined herein, in particular hydroxyl, halogen or $(C_1-C_4)$-alkoxy), aryl or aryl-$(C_1-C_4)$-alkyl (both optionally substituted in the aryl group with up to five independently selected substituents as defined herein, in particular hydroxyl, halogen, $(C_1-C_4)$-alkyl, or $(C_1-C_4)$-alkoxy, the number of said substituents being up to five for halogen, and up to three for any combination of said other substituents), as defined herein.

The term "alkylamino" represents a preferred selection of the term "amino" and refers to the group —NRR', where R and R' may independently be hydrogen or $(C_1-C_4)$alkyl.

The term "Imino" refers to the group =NR, where R may be hydrogen, alkyl (optionally substituted in the alkyl chain with up to five independently selected substituents as defined herein, in particular hydroxyl, halogen or $(C_1-C_4)$-alkoxy), aryl or aryl-$(C_1-C_4)$-alkyl (both optionally substituted in the aryl group with up to five independently selected substituents as defined herein, in particular hydroxyl, halogen, $(C_1-C_4)$-alkyl, or $(C_1-C_4)$-alkoxy, the number of said substituents being up to five for halogen, and up to three for any combination of said other substituents), as defined herein.

The term "alkylimino" represents a preferred selection of the term "imino" and refers to the group =NR, where R may be hydrogen or $(C_1-C_4)$alkyl.

The term "oxime" refers to the group =N—OR, where R may be hydrogen, alkyl (optionally substituted in the alkyl chain with up to five independently selected substituents as defined herein, in particular hydroxyl, halogen or $(C_1-C_4)$-alkoxy), aryl or aryl-$(C_1-C_4)$-alkyl (both optionally substituted in the aryl group with up to five independently selected substituents as defined herein, in particular hydroxyl, halogen, $(C_1-C_4)$-alkyl, or $(C_1-C_4)$-alkoxy, the number of said substituents being up to five for halogen, and up to three for any combination of said other substituents), as defined herein.

The term "alkyl-oxime" represents a preferred selection of the term "oxime" and refers to the group =N—O—R, where R may be hydrogen or $(C_1-C_4)$alkyl.

The term "amido" refers to the group —(C=O)—NRR', where R and R' may independently be hydrogen, alkyl (optionally substituted in the alkyl chain with up to five independently selected substituents as defined herein, in particular hydroxyl, halogen or $(C_1-C_4)$-alkoxy), aryl or aryl-$(C_1-C_4)$-alkyl (both optionally substituted in the aryl group with independently selected substituents as defined herein, in particular hydroxyl, halogen, $(C_1-C_4)$-alkyl, or $(C_1-C_4)$-alkoxy, the number of said substituents being up to five for halogen, and up to three for any combination of said other substituents), as defined herein.

The term "alkylamido" represents a preferred selection of the term "amido" and refers to the group —(C=O)—NRR', where R and R' may be independently selected from hydrogen or $(C_1-C_4)$alkyl.

The term "aryl" refers to an aromatic carbocyclic group comprising 6 to 14, more preferably 6 to 10, carbon atoms and having at least one aromatic ring or multiple condensed rings in which at least one ring is aromatic. Preferably, aryl is phenyl, naphthyl, indanyl, indenyl, fluorenyl, 1,2,3,4-tetrahydro-naphthalen-1-yl or even biphenyl.

The aryl group may optionally be substituted by substituents independently selected from the group consisting of halogen, hydroxyl, $(C_1-C_6)$alkoxy, $(C_1-C_6)$alkyl, oxo, thiol, carboxyl, aryloxy or arylalkyloxy (both optionally substituted in the aryl moiety with independently selected substituents as defined herein), $(C_1-C_6)$alkylthio, arylthio or arylalkylthio (both optionally substituted in the aryl moiety with independently selected substituents as defined herein), amino, amido, acyl, and acylamino, as defined herein, the number of said substituents being up to five for halogen, and up to three for any combination of said other substituents.

Substituted aryl is preferably substituted by substituents selected from the group consisting of $(C_1-C_6)$alkoxy, preferably methoxy, hydroxyl, $(C_1-C_4)$alkyl, halogen, the number of said substituents being up to five for halogen, and up to four, preferably up to three, for any combination of said other substituents. Preferably substituted aryl is substituted phenyl.

The term "arylalkyl" refers to an alkyl group substituted with up to three independently selected aryl groups; preferably the term "arylalkyl" refers to "aryl-$(C_1-C_4)$-alkyl" or diaryl-$(C_1-C_4)$-alkyl, whereby the aryl is an aryl group as defined above. Arylalkyl is preferably benzyl (—CH2-Phenyl) or phenethyl (—CH$_2$—CH$_2$-Phenyl).

The term "substituted arylalkyl" refers to an arylalkyl group as defined above, wherein the aryl group is substituted as defined above.

The term "pro-drug" as used herein, represents derivatives of the compounds of the invention that are drug precursors which, following administration to a patient, release the drug in vivo via a chemical or physiological process. In particular, pro-drugs are derivatives of the compounds of the invention in which functional groups carry additional substituents which may be cleaved under physiological conditions in vivo and thereby releasing the active principle of the compound (e.g., a pro-drug on being brought to a physiological pH or through an enzyme action is converted to the desired drug form).

The term "pharmaceutically acceptable salts" refers to salt forms that are pharmacologically acceptable and substantially non-toxic to the subject being administered the compounds of the invention. Pharmaceutically acceptable salts of compounds of formula I include conventional and stoichiometrical acid-addition salts or base-addition salts formed from suitable non-toxic organic or inorganic acids or inorganic bases. Acid addition salts, for example, from compounds of formula I with a basic nitrogen atom are formed preferably with organic or inorganic acids. Suitable inorganic acids are, for example, halogenic acids such as hydrochloric acid, sulfuric acid, or phosphoric acid. Suitable organic acids are, for example, carboxylic, phosphonic, or sulfonic acids, for example acetic acid, propionic acid, glycolic acid, lactic acid, hydroxybutyric acid, malic acid, malenic acid, malonic acid, salicylic acid, fumaric acid, succinic acid, adipic acid, tartaric acid, citric acid, glutaric acid, 2- or 3-glycerophosphoric acid and other mineral and carboxylic acids well known to those skilled in the art. The salts are prepared by contacting the free base forms with a sufficient amount of the desired acid to produce a salt in the conventional manner. Compounds containing acidic substituents may also form salts with inorganic or organic bases. Examples of suitable bases for salt formation include, but are not limited to, inorganic bases such as alkali or alkaline earth-metal (e.g., sodium, potassium, lithium, calcium, or magnesium) hydroxides, and those derived from ammonium hydroxides (e.g., a quaternary ammonium hydroxide such as tetramethylammonium hydroxide). Also contemplated are salts formed with pharmaceutical acceptable amines such as ammonia, alkyl amines, hydroxyalkylamines, N-methylglucamine, benzylamines, piperidines, and pyrrolidines and the like. Certain compounds will be acidic in nature, e.g. those compounds which possess a carboxyl or phenolic hydroxyl group. Salts of phenols can be made by heating acidic compounds with any of the above mentioned bases according to procedures well known to those skilled in the art.

As used herein, the term "composition" is intended to encompass a product comprising the specified ingredients in the specified amounts, as well as any product which results, directly or indirectly, from combination of the specified ingredients in the specified amounts.

The phrase "effective amount" as used herein, means an amount of a compound or composition which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of the treatment, the nature of concurrent therapy, the particular active ingredient(s) being employed, the particular pharmaceutically acceptable excipient(s)/carrier(s) utilized, and like factors within the knowledge and expertise of the attending physician.

Preferred Embodiments

According to a preferred embodiment of the present invention, the compound used for the for the manufacture of a medicament for the treatment and/or prevention of a steroid hormone dependent disease or disorder, preferably for a steroid hormone dependent disease or disorder requiring the inhibition of a 17β-hydroxysteroid dehydrogenase (17β-HSD) enzyme, most preferably requiring the inhibition of the 17β-HSD type 1, 17β-HSD type 2 or 17β-HSD type 3 enzyme, is defined as follows: the compound has the formula (II)

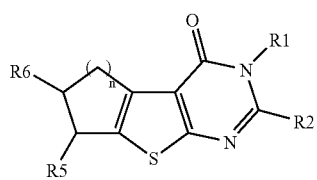

(II)

wherein $R_1$ and $R_2$ represent the same or different $C_1$-$C_8$-alkyl, or one is $C_1$-$C_8$-alkyl and the other is H, or $R_1$ and $R_2$ form together with their binding sites a cyclic 5-, 6-, 7- or 8-membered ring system, which is saturated or contains one or more double bonds between the ring atoms, and which ring optionally contains up to two N-atoms in addition to the nitrogen atom where R1 is attached, wherein said ring is optionally substituted with up to two substituents independently selected from the group consisting of alkyl, substituted alkyl, aryl, or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido;

the hydrocarbon chain —C(R5)—C(R6)—(CH)$_n$— of the ring-system adjacent to the thiophen-ring is saturated or contains one or more double bonds between the carbon atoms;

n is an integer from 1 to 4, and

R5 and R6 are individually selected from the group consisting of hydrogen, alkyl, substituted alkyl, aryl or arylalkyl, whereby the aryl group is optionally substituted, alkoxy, aryloxy, acyloxy, arylthio, alkylthio, arylsulfonyl, alkylsulfonyl, hydroxyl, oxo, halogen, amino, oxime, acyl, carboxyl, thiocarboxyl, and amido;

provided that said compound is not 1,2,7,8,9,10,11,13-octahydro-13-oxo-4-(phenylthio)-[1]benzothieno[2',3':4,5]pyrimido[1,2-a]azepine-3-carboxaldehyde;

According to a preferable embodiment the compound of the formula (II) is characterized in that the cyclic 5-, 6-, 7- or 8-membered ring system formed together by $R_1$ and $R_2$ is optionally substituted with up to two substituents independently selected from the group consisting of oxo, —CO—R, —CO—O—R, —O—R, —$C_1$-$C_4$-alkyl, optionally substituted with —O—R, —S—R or —N(R)$_2$;

R5 and R6 are individually selected from the group consisting of hydrogen, oxo, halogen, —O—R', —S—R', —SO—R', —CO—R, —CO—O—R, or —$C_1$-$C_4$-alkyl, —$C_1$-$C_4$-alkenyl or =$C_1$-$C_4$-alkylen, optionally substituted in the alkyl chain with —O—R, —S—R, —N(R)$_2$, —CO—R, or =N—O—R, wherein R represents hydrogen or $C_1$-$C_4$-alkyl; and wherein R' represents hydrogen, $C_1$-$C_8$-alkyl, which can be linear, cyclic or branched; aryl-$C_1$-$C_4$-alkyl, preferably benzyl; or aryl, preferably phenyl.

Especially preferable compounds are those wherein $R_1$ and $R_2$ form together with their binding sites an optionally substituted cyclic 5-, 6-, 7- or 8-membered ring system, which is saturated or contains one or more double bonds between the ring atoms, and which ring optionally contains up to two N-atoms in addition to the nitrogen atom where $R_1$ is attached.

Particularly preferable compounds of formula (II) are those wherein R5 is selected from the group consisting of hydrogen, oxo, halogen, —OH, —O—$C_1$-$C_4$-alkyl; —S—$C_1$-$C_4$-alkyl, —S—$C_3$-$C_8$-cycloalkyl, —S-phenyl, —SO-phenyl.

Further preferable compounds of formula (II) are those wherein R6 is selected from the group consisting of hydrogen, carbonyl, alkylcarboxyl, preferably —COOH, —$C_1$-$C_4$-alkyl, —$C_1$-$C_4$-alkenyl or =$C_1$-$C_4$-alkylen, optionally substituted in the alkyl chain with —O—R, —N(R)$_2$, —CO—R, or =N—O—R, wherein R represents hydrogen or $C_1$-$C_4$-alkyl.

In a preferred embodiment, the invention relates to a compound selected from the group consisting of exemplary compounds 2,3,8,9,10,11-Hexahydro[1]Benzothieno[2',3':4,5]pyrimido[1,2-a]azepine-4,13(1H,7H)-dione;

1,2,6,7,8,9,10-heptahydrocyclopenta[4',5]thieno[2',3':4,5]pyrimido[1,2-a]-azepin-3,12-dione;

1,2,3,4,8,9,10,11,12-nonahydrocyclohepta[4',5']thieno[2',3':4,5]pyrimido-[1,2-a]azepine-5(5aH), 14-dione;

1,2,7,8,9,10,11,12-octahydro[1]benzothieno[2',3':4,5]pyrimido-[1,2-a]azocin-4, 14(3H)-dione;

1,2,3,4,7,8,9,10-Octahydro-12H-[1]benzothieno[2,3-d]pyrido[1,2-a]pyrimidin-12-one;

5,6-Dihydro-2,3-dimethyl[1]benzothieno[2,3-d]pyrimidin-4,8(3H,7H)-dione;

5,6-Dihydro-3-methyl[1]benzothieno[2,3-d]pyrimidin-4,8 (3H,7H)-dione;

5,6-Dihydro-3-ethyl-2-methyl[1]benzothieno[2,3-d]pyrimidin-4,8(3H,7H)-dione;

4-Chloro-1,2,3,7,8,9, 10,11,12-octahydro[1]benzothieno[2',3':4,5]pyrimido-[1,2-a]-azocin-14-one-4-carboxaldehyde;

1,2,3,4,5,8,9,10,11,12-Decahydro-14H-cyclohepta[4',5']thieno[2',3':4,5]-pyrimido[1,2-a]azepin-14-one;

8-Chloro-5,6-dihydro-3-methyl[1]benzothieno[2,3-d]pyrimidin-4(3H)-one-7-carboxaldehyde;

1,2,7,8,9,10,11,13-Octahydro-13-oxo-4-(ethylthio)[1]benzothieno[2',3':4,5]-pyrimido-[1,2-a]azepine-3-carboxaldehyde;

1,2,7,8,9,10,11,13-Octahydro-13-oxo-4-(propylthio)[1]benzothieno[2',3':4,5]-pyrimido-[1,2-a]azepine-3-carboxaldehyde;

1,2,7,8,9,10,11,13-Octahydro-13-oxo-4-(butylthio)[1]benzothieno[2',3':4,5]-pyrimido-[1,2-a]azepine-3-carboxaldehyde;

1,2,7,8,9,10,11,13-Octahydro-13-oxo-4-(isopropylthio)[1]benzothieno[2',3':4,5]-pyrimido-[1,2-a]azepine-3-carboxaldehyde;

1,2,7,8,9,10,11,13-Octahydro-13-oxo-4-(t-butylthio)[1]benzothieno[2',3':4,5]-pyrimido-[1,2-a]azepine-3-carboxaldehyde;

1,2,7,8,9,10,11,13-Octahydro-13-oxo-4-(cyclopentylthio)[1]benzothieno[2',3':4,5]-pyrimido-[1,2-a]azepine-3-carboxaldehyde;

1,2,7,8,9,10,11,13-Octahydro-13-oxo-4-(cyclohexylthio)[1]benzothieno[2',3':4,5]-pyrimido-[1,2-a]azepine-3-carboxaldehyde;

1,2,7,8,9,10,11,13-Octahydro-13-oxo-4-(phenylthio)[1]benzothieno[2',3':4,5]-pyrimido-[1,2-a]azepine-3-hydroxymethyl;

1,2,7,8,9,10,11,13-Octahydro-13-oxo-4-(cyclohexylthio)[1]benzothieno-[2',3':4,5]pyrimido [1,2-a]azepine-3-hydroxymethyl;

Octahydro-13-oxo-4-(phenylthio)[1]benzothieno[2',3':4,5]-pyrimido-[1,2-a]azepine-3-oxime-methyl;

4-Chloro-1,2,7,8,9,10,11,13-octahydro-13-oxo[1]benzothieno[2',3':4,5]-pyrimido[1,2-a]azepine-3-hydroxymethyl;

3-N,N-Dimethylamino-methylen-2,3,8,9,10,11-hexahydro[1]benzothieno[2',3':4,5]pyrimido[1,2-a]azepine-4,13 (1H,7H)-dione;

1,2,7,8,9,10,11,13-Octahydro-13-oxo-4-(propylthio)[1]benzothieno[2',3':4,5]-pyrimido-[1,2-a]azepine-3-(3-oxo)but-1-ene; and 1,2,7,8,9,10,11,13-Octahydro-13-oxo-4-(butylthio)[1]benzothieno[2',3':4,5]-pyrimido-[1,2-a]azepine-3-(3-oxo)but-1-ene, or a physiologically acceptable salt thereof.

Pharmaceutically acceptable salts of the compounds of the invention as well as commonly used pro-drugs and active metabolites of these compounds are also within the scope of the invention.

The invention also relates to pharmaceutical compositions comprising one or more of the compounds of the invention for which no use in therapy has been disclosed earlier, or their salts or pro-drugs, as active agent and at lease one pharmaceutically acceptable carrier.

Furthermore, the invention relates to the use of an effective amount of a novel compound as defined herein for the treatment or prevention of a steroid hormone dependent disease or disorder in a mammal, in particular a human. Preferably the steroid hormone dependent disease or disorder is an estradiol or testosterone dependent disease or disorder.

In a preferred embodiment, the invention relates to the use of an effective amount of a novel compound as defined within the present invention for the treatment or prevention of a steroid hormone dependent disease or disorder in a mammal, whereby the steroid hormone dependent disease or disorder requires the inhibition of a 17β-hydroxysteroid dehydrogenase (HSD) enzyme, preferably the human 17β-hydroxysteroid dehydrogenase (HSD) enzyme type 1, type 2 or type 3.

In a further preferred embodiment of the invention the steroid hormone dependent disease or disorder to be treated and/or prevented requires the lowering of the endogenous 17β-estradiol or testosterone concentration in a generalized and/or tissue specific manner.

The invention also relates to a method of treating a mammal such as a human having a condition related to 17β-hydroxysteroid dehydrogenase (HSD) type 1, type 2 or type 3 activity, comprising administering to the mammal an amount of a compound of this invention, or a salt or a prodrug thereof, which amount is effective to treat the condition. Administration of compounds of this invention in combination with other pharmaceuticals used in treatment of the listed conditions is contemplated.

The conditions to be treated and/or prevented in the context of the present invention include but are not limited to breast cancer, prostate carcinoma, ovarian cancer, uterine cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, prostatitis, acne, seborrhea, hirsutism, androgenic alopecia, precocious puberty, adrenal hyperplasia, polycystic ovarian syndrome, and urinary dysfunction. A further condition to be treated and/or prevented in the context of the present invention includes osteoporosis.

Further estrogen-dependent diseases which may be treated and/or prevented with an effective amount of a compound of the invention are multiple sclerosis, rheumatoid arthritis, Alzheimer's disease, colon cancer, tissue wounds, skin wrinkles and cataracts.

In a preferred embodiment the invention relates to use of an effective amount of a compound of the invention for the treatment or prevention of one of the aforementioned disease or disorders in a mammal whereby the mammal is a human, preferably a female and most preferably a pre- or peri-menopausal female in the case of gynaecological disorders.

Furthermore, compounds of formula (I) may be useful for blocking spermatogenesis and as an anti-fertility agent for males.

The disclosed compounds are also useful as diagnostic agents (e.g. in diagnostic kits or for use in clinical laboratories) for screening for the presence or absence of 17β-hydroxysteroid dehydrogenase (HSD) type 1, type 2 and/or type 3 activity.

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

Administration Forms

The method of the invention is primarily intended for treatment in a mammal, preferably in humans and other primates, of steroid hormone dependent diseases or disorders, in particular estradiol dependent diseases or disorders, wherein the steroid hormone dependent disease or disorder preferably requires the inhibition of a 17β-hydroxysteroid dehydrogenase (HSD) enzyme, preferably the type 1 17β-hydroxysteroid dehydrogenase (HSD) enzyme [EC 1.1.1.62].

The compounds may be administered orally, dermally, parenterally, by injection, by pulmonal or nasal delivery, or sublingually, rectally or vaginally in dosage unit formulations. The term "administered by injection" includes intravenous, intraarticular, intramuscular (e.g. by depot injection where the active compounds are released slowly into the blood from the depot and carried from there to the target organs), intraperitoneal, intradermal, subcutaneous, and intrathecal injections, as well as use of infusion techniques. Dermal administration may include topical application or transdermal administration. One or more compounds may be present in association with one or more non-toxic pharmaceutically acceptable auxiliaries such as excipients, adjuvants (e.g. buffers), carriers, inert solid diluents, suspensing agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated for example as immediate release, sustained release, pulsatile release, two or more step release, depot or other kind of release formulations.

The manufacture of the pharmaceutical compositions according to the invention may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc. Suitable auxiliaries and further ingredients may be such as recommended for pharmacy, cosmetics and related fields and which preferably are listed in the European Pharmacopoeia, FDA approved or cited in the "GRAS" list (FDA List of food additives that are 'generally recognized as safe' (GRAS)).

One mode of application of the compounds of general formula (I) or of pharmaceutical compositions comprising one or more of said compounds is oral application, e.g., by tablets, pills, dragees, hard and soft gel capsules, granules, pellets, aqueous, lipid, oily or other solutions, emulsions such as oil-in-water emulsions, liposomes, aqueous or oily suspensions, syrups, elixiers, solid emulsions, solid dispersions or dispersible powders. For the preparation of pharmaceutical compositions for oral administration, the compounds suitable for the purposes of the present invention as defined above can be admixed with commonly known and used adjuvants and excipients such as for example, gum arabic, talcum, starch, sugars (such as, e. g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the active ingredients may also be dispersed in a microparticle, e.g. a nanoparticulate, composition.

For parenteral administration, the active agents can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration the active agent can be in the form of an aqueous, lipid, oily or other kind of solution or suspension or even administered in the form of liposomes or nano-suspensions.

Transdermal application can be accomplished by suitable patches, as generally known in the art, specifically designed for the transdermal delivery of active agents, optionally in the presence of specific permeability enhancers. Furthermore, also emulsions, ointments, pastes, creams or gels may be used for transdermal delivery.

Another suitable mode of administration is via intravaginal devices (e.g. vaginal rings) or intrauterine systems (IUS) containing reservoirs for controlled release of active agents over extended periods of time. For rectal or vaginal administration of the drug the compounds may also be administered in the form of suppositories. These compositions can be prepared by mixing the drug with a suitable non-irritating excipient which is solid at ordinary temperatures but liquid at the rectal or vaginal temperature and will therefore melt in the rectum or vagina to release the drug.

Another mode of application is by implantation of a depot implant comprising an inert carrier material, such as biologically degradable polymers or synthetic silicones such as e.g. silicone rubber. Such implants are designed to release the active agent in a controlled manner over an extended period of time (e.g., 3 to 5 years).

It will be appreciated by those skilled in the art that the particular method of administration will depend on a variety of factors, all of which a reconsidered routinely when administering therapeutics.

The actually required dosages of the agents of this invention for any given patient will depend upon a variety of factors, including, but not limited to the activity of the specific compound employed, the particular HSD type 1, type 2 or type 3 related condition being treated, the particular composition formulated, the mode of administration, time and duration of administration, route of administration and the particular site being treated, and furthermore the age of the patient, the body weight of the patient, the general health of the patient, the gender of the patient, the diet of the patient, rate of excretion, drug combinations, and the severity of the condition undergoing therapy.

It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests. Optimal dosages for a given set of conditions may be ascertained by those skilled in the art using conventional dosage-determination tests in view of the experimental data for a given compound. For oral administration, an exemplary daily dose generally employed will be from about 0.01 µg/kg to about 100 mg/kg of total body weight, whereby courses of treatment may be repeated at appropriate time intervals. Administration of pro-drugs may be dosed at weight levels that are chemically equivalent to the weight levels of the fully active compounds. The daily dosage for parenteral administration will generally be from about 0.01 µg/kg to about 100 mg/kg of total body weight. A daily rectal dosage regimen will generally be from about 0.01 µg/kg to about 200 mg/kg of total body weight. A daily vaginal dosage regimen will generally be from about 0.01 µg/kg to about 100 mg/kg of total body weight. The daily topical dosage regimen will generally be from about 0.1 µg to about 100 mg administered between one to four times daily. The transdermal concentration will generally be that required to maintain a daily dose of from 0.01 µg/kg to 100 mg/kg of total body weight.

Abbreviations and Acronyms

As employed herein, the following terms have the indicated meanings:

20βP 20β-hydroxyprogesterone
A 4-androstene-3,17-one
Ac Acetyl
AcOH acetic acid
HSD hydroxysteroid dehydrogenase
DHT dehydrotestosterone
DMF N,N-dimethylformamide E1 estron
E2 estradiol
ER estrogen receptor
EtOAc ethyl acetate
GnRH Gonadotropin Releasing Hormone
GRAS generally recognized as safe
MS mass spectrometry
NAD(P)[H] nicotinamide-adenine-dinucleotide (phosphate) [reduced NAD(P)]
NMR nuclear magnetic resonance
P progesterone PCC pyridinium chlorochromate
T testosterone
TBAB Tetrabutylammonium Bromide
THF tetrahydrofuran
TOF 'Time-of-flight'

Experimental Section

General Preparative Methods

The compounds of the present invention may be prepared by use of known chemical reactions and procedures. Nevertheless, the following general preparative methods are presented to aid the reader in synthesizing the 17-β-hydroxysteroid dehydrogenase inhibitors with specific details provided below in the experimental section to illustrate working examples.

All variable groups of these methods are as described in the generic description if they are not specifically defined below.

It is recognized that compounds of the invention with each claimed optional functional group may not be prepared by each of the below-listed methods. Within the scope of each method, optional substituents may appear on reagents or intermediates which may act as protecting or otherwise non-participating groups. Utilizing methods well known to those skilled in the art, these groups are introduced and/or removed during the course of the synthetic schemes which provide the compounds of the present invention.

The compounds according to this invention can be prepared as shown in Schemes 2 to 6 described in the Experimental section. It is evident that otherwise ring-substituted or -modified compounds as defined by formula (I) of the claims can be prepared analogously, e.g. by using ring-substituted or -modified analogues of the starting compound (2) in Scheme 1.

The invention will be illuminated by the following non-restrictive Experimental Section. In order to more fully illustrate the nature of the invention and the manner of practicing the same, the following examples are presented, but they should not be taken as limiting.

EXAMPLE 1

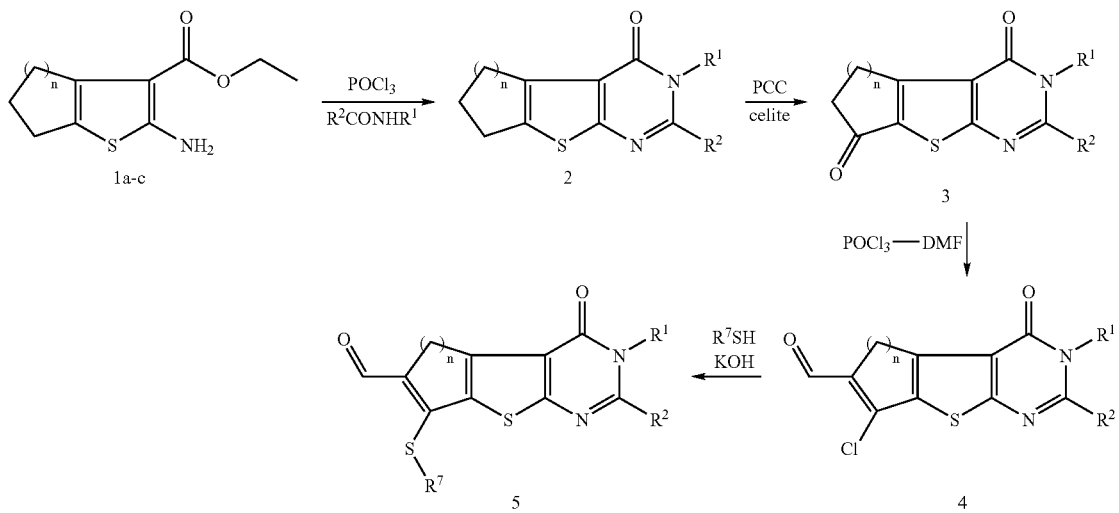

Scheme 1. Synthesis of compound classes 2-5

TABLE 1

Individual compounds of compound classes 2-4 prepared

| compound | N | R¹ | R² |
|---|---|---|---|
| 2a | 2 |  | —(CH$_2$)$_5$— |
| 2b | 1 |  | —(CH$_2$)$_5$— |
| 2c | 3 |  | —(CH$_2$)$_5$— |
| 2d | 2 |  | —(CH$_2$)$_6$— |
| 2e | 2 |  | —(CH$_2$)$_4$— |
| 2f | 2 |  | —(CH$_2$)$_3$— |
| 2g | 2 | —CH$_3$ | —CH$_3$ |
| 2h | 2 | —CH$_3$ | H |
| 2i | 2 | —CH$_3$ | —CH$_2$CH$_3$ |
| 3a | 2 |  | —(CH$_2$)$_5$— |
| 3b | 1 |  | —(CH$_2$)$_5$— |
| 3c | 3 |  | —(CH$_2$)$_5$— |
| 3d | 2 |  | —(CH$_2$)$_6$— |
| 3e | 2 |  | —(CH$_2$)$_4$— |
| 3f | 2 |  | —(CH$_2$)$_3$— |
| 3g | 2 | —CH$_3$ | —CH$_3$ |
| 3h | 2 | —CH$_3$ | H |
| 3i | 2 | —CH$_3$ | —CH$_2$CH$_3$ |
| 4a | 2 |  | —(CH$_2$)$_5$— |
| 4b | 2 |  | —(CH$_2$)$_6$— |
| 4c | 2 |  | —(CH$_2$)$_3$— |
| 4d | 3 |  | —(CH$_2$)$_5$— |
| 4e | 2 | —CH$_3$ | H |

General Procedure for the Synthesis of 2a-i:

2a 2,3,4,7,8,9,10,11-Octahydro[1]benzothieno[2',3':4,5]pyrimido-[1,2-a]azepin-13(1H)-one:

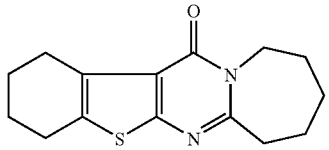

To ethyl 2-amino-4,5,6,7-tetrahydrobenzo(b)thiophene-3-carboxylate 1b (0.22 mol) and ε-caprolactam (0.33 mol) in dry dichloroethane (1500 ml), POCl$_3$ (0.27 mol) was added dropwise.

The mixture was heated under reflux until no starting material was detected on TLC after which ⅘ of the solvent was evaporated. Water (200 ml) was added and the solution was made basic with 20% KOH. The solution was extracted with CH$_2$Cl$_2$, washed with brine and water and dried with Na$_2$SO$_4$. After filtration the solvent was evaporated. Recrystallisation from ethanol afforded 2a as white crystals in 90% yield.

$^1$H NMR δ 1.85 (10H, m), 2.75 (2H, m), 3.00 (4H, m), 4.35 (2H, m)

2b 1,2,3,6,7,8,9,10-Octahydro-12H-cyclopenta[4',5']thieno[2',3':4,5]pyrimido[1,2-a]-azepin-12-one

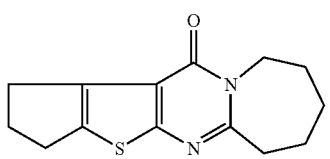

2b was synthesised as described above but ethyl 2-aminocyclopenta(b)-thiophene-3-carboxylate was used.

$^1$H NMR δ 1.83 (8H, m), 2.45 (2H, qn), 3.00 (4H, m), 4.37 (2H, m)

2c 1,2,3,4,5,8,9,10,11,12-Decahydro-14H-cyclohepta[4',5']thieno[2',3':4,5]pyrimido-[1,2-a]azepin-14-one

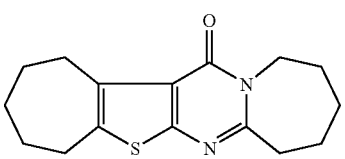

2c was synthesised as described above but ethyl 2-aminocyclo-hepta(b)thiophene-3-carboxylate was used.

$^1$H NMR δ 1.77 (12H, m), 2.82 (2H, m), 3.01 (2H, m), 3.35 (2H, m), 4.36 (2H, m)

2d 2,3,4,7,8,9,10,11,12-Decahydro[1]benzothieno[2',3':4,5]pyrimido-[1,2-a]azocin-14(1H)-one

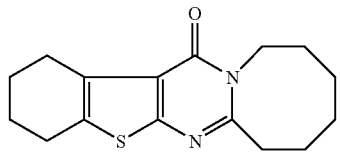

2d was synthesised as described above but 2-azacyclooctanone was used.

$^1$H NMR δ1.40 (2H, m), 1.56 (2H, m), 1.89 (8H, m), 2.76 (2H, m), 2.99 (4H, m), 4.27 (2H, m)

2e 1,2,3,4,7,8,9,10-Octahydro-12H-[1]benzothieno[2,3-d]pyrido[1,2-a]pyrimidin-12-one

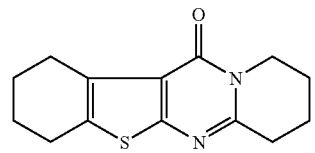

2e was synthesised as described above but δ-valerolactam was used.

$^1$H NMR δ 1.91 (8H, m), 2.75 (2H, m), 2.97 (4H, m), 4.02 (2H, t)

2f 2,3,6,7,8,9-Hexahydro[1]benzothieno[2,3-d]pyrrolo[1,2-a]pyrimidin-10(1H)-one

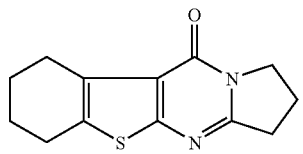

2f was synthesised as described above but 2-pyrrolidinone was used.

$^1$H NMR δ 1.86 (4H, m), 2.28 (2H, qn), 2.76 (2H, m), 3.00 (2H, m), 3.14 (2H, t), 4.16 (2H, t)

2g 5,6,7,8-Tetrahydro-2,3-dimethyl[1]benzothieno[2,3-d]pyrimidin-4(3H)-one

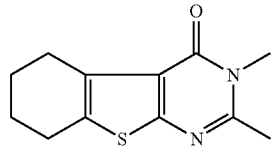

2g was synthesised as described above but N-methylacetamide was used.

$^1$H NMR δ 1.86 (4H, m), 2.58 (3H, s), 2.76 (2H, m), 3.00 (2H, m), 3.56 (3H, m)

2h 5,6,7,8-Tetrahydro-3-methyl[1]benzothieno[2,3-d]pyrimidin-4(3H)-one

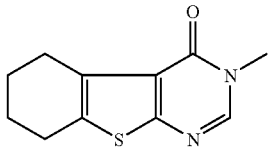

2h was synthesised as described above but acetamide was used.

$^1$H NMR δ 1.87 (4H, m), 2.78 (2H, m), 3.03 (2H, m), 3.56 (3H, s), 7.91 (1H, s)

2i 5,6,7,8-Tetrahydro-2-ethyl-3-methyl[1]benzothieno[2,3-d]pyrimidin-4(3H)-one

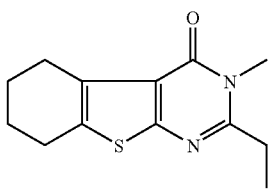

2i was synthesised as described above but N-methylpropanamide was used.

$^1$H NMR δ 1.36 (3H, t), 1.85 (4H, m), 2.78 (4H, m), 3.01 (2H, m), 3.57 (3H, s)

General procedure for the synthesis of 3a-i: PCC (37 mmol), Celite (20 g) and compound 2a (7.3 mmol) were mix into a fine powder and dry benzene (150 ml) was added. The reaction mixture was heated under refluxed over night. The cooled slurry was filtrated through a pad of Celite and the solvent was evaporated. Recrystallisation from methanol afforded white powder in 50% yield.

3a 2,3,8,9,10,11-Hexahydro[1]Benzothieno[2',3':4,5]pyrimido[1,2-a]azepine-4,13(1H,7H)-dione

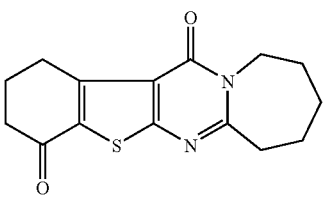

$^1$H NMR δ 1.58 (6H, m), 2.23 (2H, qn), 2.67 (2H, t), 3.07 (2H, m), 3.28 (2H, t), 4.36(2H, m)

3b 1,2,6,7,8,9,10-heptahydrocyclopenta[4',5']thieno[2',3':4,5]pyrimido[1,2-a]-azepin-3,12-dione

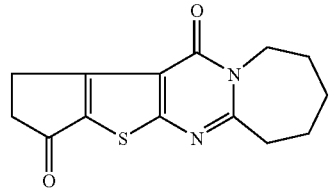

$^1$H NMR δ 1.88 (4H, m), 2.92 (2H, m), 3.09 (2H, m), 3.33 (2H, m), 4.39 (2H, m)

3c 1,2,3,4,8,9,10,11,12-nonahydrocyclohepta[4',5']thieno[2',3':4,5]pyrimido-[1,2-a]azepine-5(5aH),14-dione

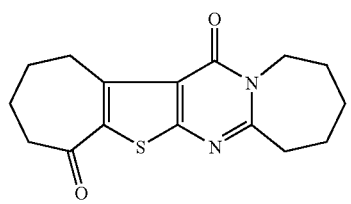

$^1$H NMR δ 1.90 (12H, m), 2.83 (2H, m), 3.05 (2H, m), 3.57 (2H, m), 4.36 (2H, m)

3d 1,2,7,8,9,10,11,12-octahydro[1]benzothieno[2',3':4,5]pyrimido-[1,2-a]azocin-4, 14(3H)-dione

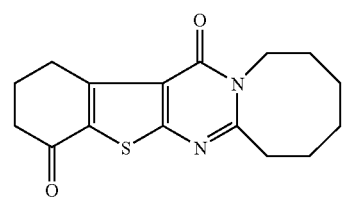

$^1$H NMR δ 1.45 (2H, m), 1.61 (2H, m), 1.97 (4H, m), 2.24 (2H, qn), 2.67 (2H, m), 3.02 (2H, m), 3.29 (2H, t), 4.31 (2H, m)

3e 1,2,3,4,7,8,9,10-Octahydro-12H-[1]benzothieno[2,3-d]pyrido[1,2-a]pyrimidin-12-one

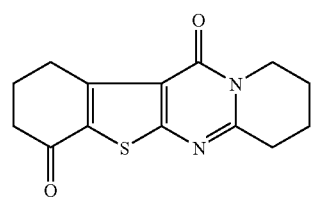

$^1$H NMR δ 1.99 (4H, m), 2.23 (2H, qt), 2.66 (2H, t), 3.01 (2H, t), 3.28 (2H, t), 4.03 (2H, t)

3f 2,3,8,9-Tetrahydro[1]benzothieno[2,3-d]pyrrolo[1,2-a]pyrimidine-6,10(1H,7H)-dione

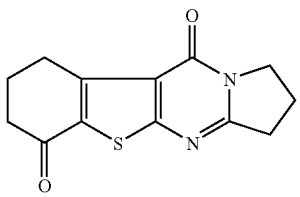

¹H NMR δ 2.29 (4H, m), 2.67 (2H, t), 3.24 (4H, m), 4.19 (2H, t)

3g 5,6-Dihydro-2,3-dimethyl[1]benzothieno[2,3-d]pyrimidin-4,8(3H,7H)-dione

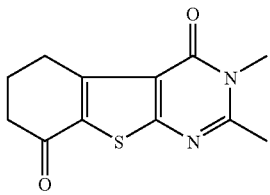

¹H NMR δ 2.24 (2H, qn), 2.63 (3H, s), 2.66 (2H, m), 3.28 (2H, t), 3.59 (3H, s)

3h 5,6-Dihydro-3-methyl[1]benzothieno[2,3-d]pyrimidin-4,8(3H,7H)-dione

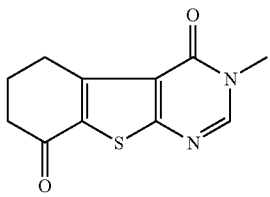

¹H NMR δ 2.25 (2H, qn), 2.69 (2H, t), 3.31 (2H, t), 3.60 (3H, s), 8.08 (1H, s)

3i 5,6-Dihydro-3-ethyl-2-methyl[1]benzothieno[2,3-d]pyrimidin-4,8(3H,7H)-dione

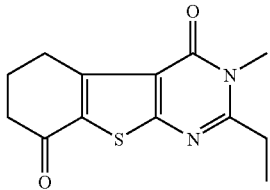

¹H NMR δ 1.39 (3H, t), 2.23 (2H, qn), 2.67 (2H, m), 2.81 (2H, q), 3.29 (2H, t), 3.59 (3H, s)

General procedure for the synthesis of 4a-4e: POCl₃ (135 mmol) was added dropwise into DMF (170 mmol) and CH₂Cl₂ (3 ml) at 0° C. After 30 minutes 3a (17 mmol) in CH₂Cl₂ (15 ml) was added dropwise. The reaction mixture was allowed to reach room temperature and stirred for 48h. The reaction was quenched with satured NaOAc, extracted with CH₂Cl₂, washed with brine and water, and dried with Na₂SO₄. After filtration the solvent was evaporated. The product was purified by flash chromatography using CH₂Cl₂-EtOAc 9:1 as an eluent. Recrystallisation from ethanol afforded 4a as yellow crystals in 75% yield.

4a 4-Chloro-1,2,7,8,9,10,11,13-octahydro-13-oxo[1]benzothieno[2',3':4,5]pyrimido[1,2-a]azepine-3-carboxaldehyde

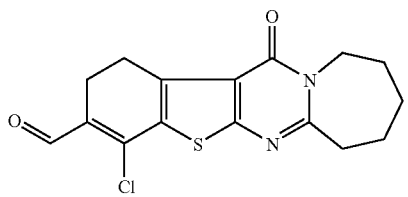

¹H NMR δ 1.86 (2H, m), 2.81 (2H, dt), 3.07 (2H, m), 3.28 (2H, dt), 4.37 (2H, m), 10.21 (1H, s)

4b 4-Chloro-1,2,3,7,8,9, 10,11,12-octahydro[1]benzothieno[2',3':4,5]pyrimido-[1,2-a]-azocin-14-one-4-carboxyaldehyde:

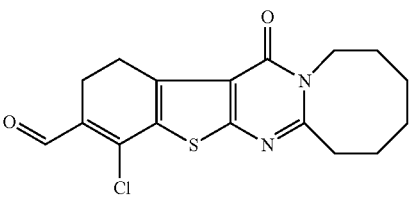

Purification by flash chromatography afforded compound 4b as a major product and compound 11 as a minor product.

¹H NMR δ 1.44 (2H, m), 1.60 (2H, m), 1.93 (4H, m), 2.76 (2H, m), 3.02 (2H, m), 3.28 (2H, m), 4.31 (2H, m), 10.21 (1H, s)

11 4-Chloro-1,2,7,9, 10,11,12,14-octahydro-14-oxo-8H-[1]benzothieno[2',3':4,5]pyrimido-[1,2-a]-azocine-3,7-dicarbaldehyde

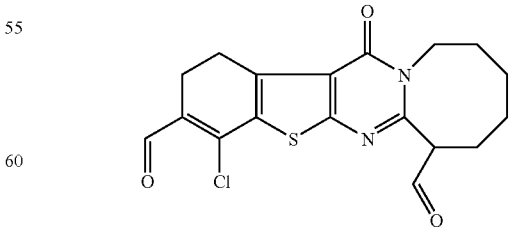

¹H NMR δ (CDCl₃) 1.31 (2H, m), 1.82 (5H, m), 2.43 (1H, m), 2.81 (2H, t) 3.29 (2H, m), 3.75 (2H, m), 4.93 (1H, m), 9.92 (1H, s), 10.21 (1H, s)

4c 8-Chloro-4-oxo-1,2,3,4,8,9-hexahydro[1]benzothieno[2,3-d]pyrrolo[1,2-a]pyrimidine-7-carbaldehyde

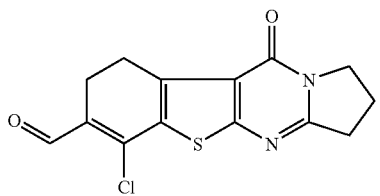

$^1$H NMR δ 2.33 (2H, m), 2.81 (2H, m), 3.25 (4H, m), 4.20 (2H, m), 10.20 (1H, s)

4d 1,2,3,4,5,8,9,10,11,12-Decahydro-14H-cyclohepta[4',5]thieno[2',3':4,5]-pyrimido[1,2-a]azepin-14-one

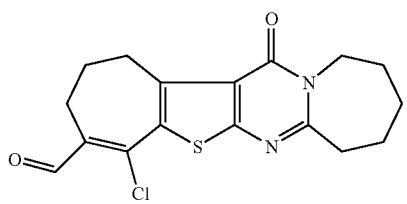

$^1$H NMR δ 2.82 (2H, m), 3.31 (2H, m), 3.60 (3H, s), 8.04 (1H, s), 10.22 (1H, s)$^1$H NMR δ 2.82 (2H, m), 3.31 (2H, m), 3.60 (3H, s), 8.04 (1H, s), 10.22 (1H, s)

4e 8-Chloro-5,6-dihydro-3-methyl[1]benzothieno[2,3-d]pyrimidin-4(3H)-one-7-carboxyaldehyde

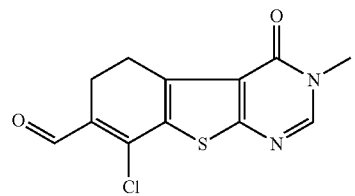

$^1$H NMR δ 2.81 (2H, m), 3.31 (2H, m), 3.59 (3H, s), 8.03 (1H, s), 10.22 (1H, s)

TABLE 2

Individual compounds of compound class 5 prepared.

| compound | n | $R^1$ | $R^2$ | $R^7$ |
|---|---|---|---|---|
| 5a | 2 | —(CH$_2$)$_5$— | | —Ph |
| 5b | 2 | —(CH$_2$)$_5$— | | —CH$_2$CH$_3$ |
| 5c | 2 | —(CH$_2$)$_5$— | | —CH$_2$CH$_2$CH$_3$ |
| 5d | 2 | —(CH$_2$)$_5$— | | —CH$_2$CH$_2$CH$_2$CH$_3$ |
| 5e | 2 | —(CH$_2$)$_5$— | | —CH(CH$_3$)$_2$ |
| 5f | 2 | —(CH$_2$)$_5$— | | —C(CH$_3$)$_3$ |
| 5g | 2 | —(CH$_2$)$_5$— | | cyclopentyl |
| 5h | 2 | —(CH$_2$)$_5$— | | cyclohexyl |
| 5i | 2 | —(CH$_2$)$_6$— | | —CH$_2$CH$_2$CH$_3$ |

General procedure for the synthesis of 5a-5h: 4a (0.62 mmol) in THF (20 ml) followed by 1 M NaOH (0.93 ml) were added dropwise into thiophenol (1.06 mmol) in THF (2 ml) at −18° C. The reaction mixture was allowed to reach room temperature and stirred until no starting material was detected on TLC. Reaction mixture was poured into large excess of water and stirred for 1 h. The product was filtrated and recrystallisation afforded 5a as yellow crystals in 85% yield.

5a 1,2,7,8,9,10,11,13-Octahydro-13-oxo-4-(phenylthio)[1]benzothieno[2',3':4,5]-pyrimido-[1,2-a]azepine-3-carboxaldehyde

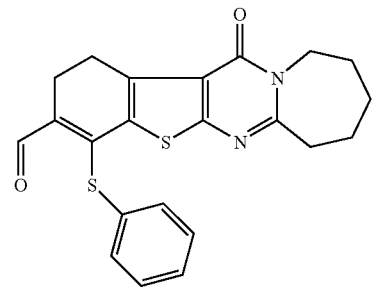

$^1$H NMR δ 1.77 (6H, m), 2.82 (2H, m), 2.95 (2H, m), 3.25 (2H, m), 4.29 (2H, m), 7.23 (5H, m), 10.47 (1H, s)

5b 1,2,7,8,9,10,11,13-Octahydro-13-oxo-4-(ethylthio)[1]benzothieno[2',3':4,5]-pyrimido-[1,2-a]azepine-3-carboxaldehyde

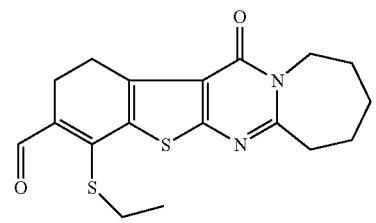

5b was synthesised as described above but ethanethiol was used.

$^1$H NMR δ 1.26 (3H, t), 1.85 (6H, m), 2.76 (2H, m), 2.91 (2H, q), 3.07 (2H, m), 3.22 (2H, m), 4.37 (2H, m), 10.48 (1H, s). M/z 360

5c 1,2,7,8,9,10,11,13-Octahydro-13-oxo-4-(propylthio)[1]benzothieno[2',3':4,5]-pyrimido-[1,2-a]azepine-3-carboxaldehyde

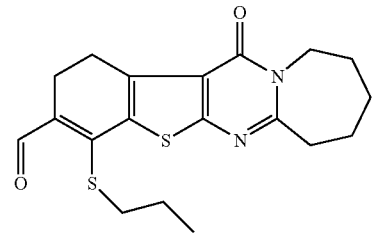

5c was synthesised as described above but propanethiol was used.

$^1$H NMR δ 0.99 (3H, t), 1.63 (2H, m), 1.86 (6H, m), 2.76 (2H, m), 2.87 (2H, t), 3.06 (2H, m), 3.22 (2H, m), 4.37 (2H, m), 10.49 (1H, s). M/z 374

5d 1,2,7,8,9,10,11,13-Octahydro-13-oxo-4-(butylthio)[1]benzothieno[2',3':4,5]-pyrimido-[1,2-a]azepine-3-carboxaldehyde

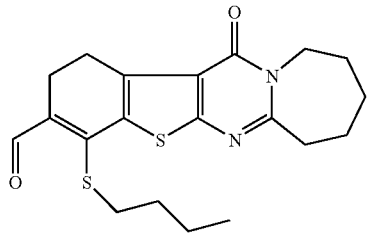

5d was synthesised as described above but butanethiol was used.

$^1$H NMR δ 0.89 (3H, t), 1.46 (4H, m), 1.86 (6H, m), 2.76 (2H, m), 2.89 (2H, t), 3.06 (2H, m), 3.22 (2H, m), 4.37 (2H, m), 10.48 (1H, s). M/z 388

5e 1,2,7,8,9,10,11,13-Octahydro-13-oxo-4-(isopropylthio)[1]benzothieno[2',3':4,5]-pyrimido-[1,2-a]azepine-3-carboxaldehyde

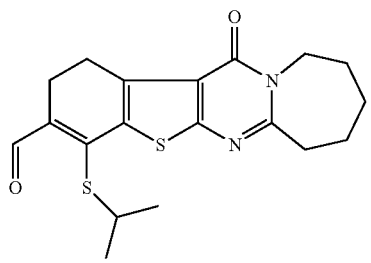

5e was synthesised as described above but 2-propanethiol was used.

$^1$H NMR δ 1.31 (6H, d), 1.85 (6H, m), 2.77 (2H, m), 3.06 (2H, m), 3.23 (2H, m) 3.41 (1H, septet), 4.37 (2H, m), 10.47 (1H, m). M/z 374

5f 1,2,7,8,9,10,11,13-Octahydro-13-oxo-4-(t-butylthio)[1]benzothieno[2',3':4,5]-pyrimido-[1,2-a]azepine-3-carboxaldehyde

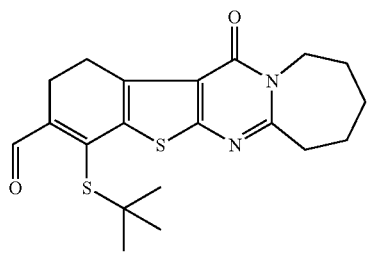

$^1$H NMR δ 1.37 (9H, s), 1.86 (6H, m), 2.80 (2H, t), 3.06 (2H, m), 4.37 (2H, m), 10.42 (1H, s)

5g 1,2,7,8,9,10,11,13-Octahydro-13-oxo-4-(cyclopentylthio)[1]benzothieno[2',3':4,5]-pyrimido-[1,2-a]azepine-3-carboxaldehyde

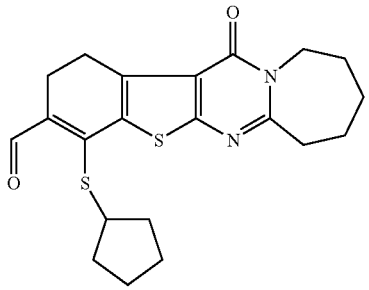

$^1$H NMR δ 1.60-1.85 (14H, m), 2.76 (2H, t), 3.22 (2H, t), 3.61 (1H, m), 4.37 (2H, m), 10.46 (1H, s)

5h 1,2,7,8,9,10,11,13-Octahydro-13-oxo-4-(cyclohexylthio)[1]benzothieno[2',3':4,5]-pyrimido-[1,2-a]azepine-3-carboxaldehyde

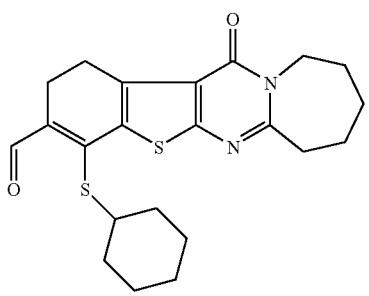

$^1$H NMR δ $^1$H NMR δ 1.25-1.99 (16H, m), 2.77 (2H, m), 3.06-3.27 (5H, m), 4.36 (2H, m), 10.47 (1H, s)

5i 1,2,7,9,10,11,12,14-octahydro-14-oxo-4-(propylthio)-8H-[1]benzothieno[2',3':4,5]pyrimido-[1,2-a]-azocine-3-carbaldehyde

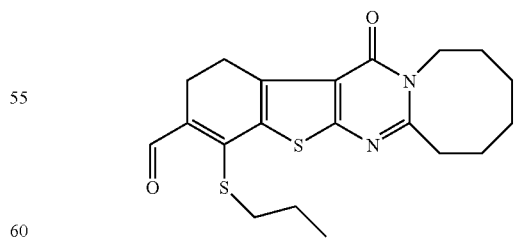

Compound 5i was synthesized as compound 5c using 4b as a starting material.

$^1$H NMR (CDCl$_3$) δ 0.99 (3H, t), 1.44 (2H, m), 1.62 (4H, m), 1.93 (4H, m), 2.76 (2H, m), 2.87 (2H, m), 3.02 (2H, m), 3.22 (2H, m), 4.30 (2H, broad s), 10.49 (1H, s)

EXAMPLE 2

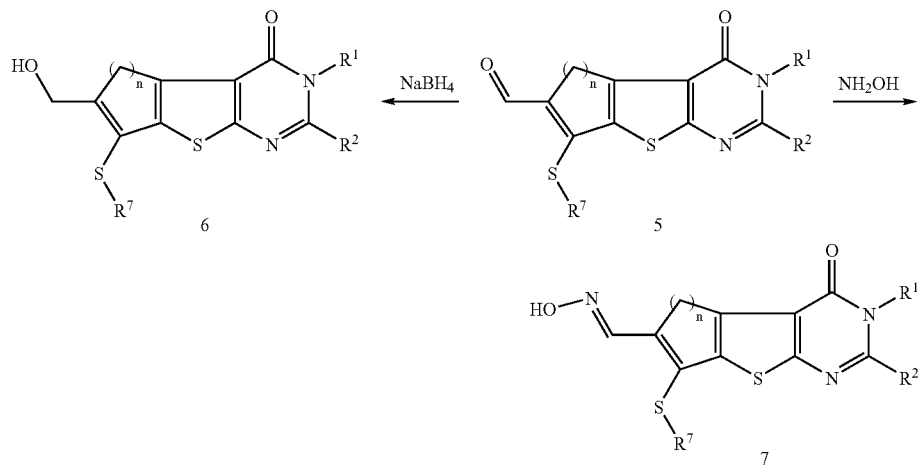

Scheme 2. Synthesis of compounds 6 and 7.

TABLE 3

| compound | n | R¹ | R² | R⁷ |
|---|---|---|---|---|
| 6a | 2 | —(CH$_2$)$_5$— | | —Ph |
| 6b | 2 | —(CH$_2$)$_5$— | | cyclohexyl |
| 6c | 2 | —(CH$_2$)$_5$— | | propyl |
| 7 | 2 | —(CH$_2$)$_5$— | | —Ph |

General procedure for the synthesis of 6a-6b and 8: NaBH$_4$ (0.66 mmol) was added into 5a (0.52 mmol) in ethanol (300 ml). After stirring for 20 minutes water (65 ml) was added followed by acidification with HCl. Ethanol was evaporated and the product was filtered affording 6a as pale yellow powder in 98% yield.

6a 1,2,7,8,9,10,11,13-Octahydro-13-oxo-4-(phenylthio)[1]benzothieno[2',3':4,5]-pyrimido-[1,2-a]azepine-3-hydroxymethyl

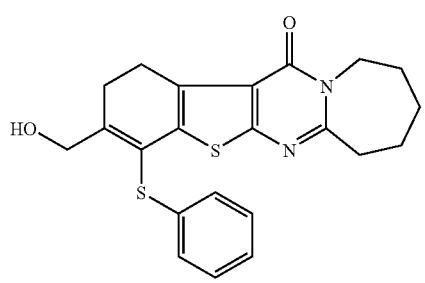

$^1$H NMR δ 1.80 (6H, m), 2.79 (2H, m), 2.99 (2H, m), 3.29 (2H, m), 4.33 (2H, m), 4.61 (2H, s), 7.17 (5H, m). M/z 410

6b 1,2,7,8,9,10,11,13-Octahydro-13-oxo-4-(cyclohexylthio)[1]benzothieno-[2',3':4,5]pyrimido [1,2-a]azepine-3-hydroxymethyl

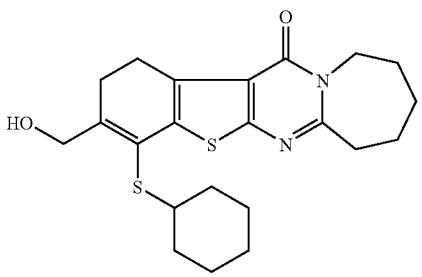

$^1$H NMR δ 1.22-1.92 (16H, m), 2.66 (2H, m), 2.9-3.1 (3H, m), 3.21 (2H, m), 4.36 (2H, m) 4.59 (2H, s)

6c 1,2,8,9,10,11-Hexahydro-3-(hydroxymethyl)-4-(propylthio)-[1]benzothieno[2',3':4,5]-pyrimido-[1,2-a]azepine-13(7H)-one

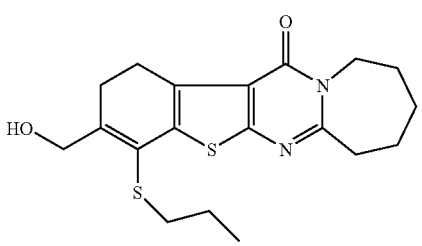

Compound 6c was synthesised by the method described for 6a-b using compound 5c as a starting material.

$^1$H NMR (D$_6$-acetone) δ 0.96 (3H, t), 1.60 (2H, m), 1.84 (6H, m), 2.68 (4H, m), 3.10 (4H, m), 4.38 (2H, m), 4.57 (2H, broad s)

MS (m/z) 376

Synthesis of 7: NaOAc (0.50 mmol) was added to NH₂OH.HCl (0.50 mmol) in absolute ethanol (3 ml) at 0° C., followed by addition of 5a (0.26 mmol) in dry THF (7 ml). The reaction mixture was allowed to reach room temperature and stirred for over night. The reaction was quenched with water, extracted with CH₂Cl₂, washed with brine and water, and dried with Na₂SO₄. After filtration solvent was evaporated giving 7 in 95% yield. Recrystallisation from ethanol afforded pale yellow powder.

7  Octahydro-13-oxo-4-(phenylthio)[1]benzothieno[2',3':4,5]-pyrimido-[1,2-a]azepine-3-oxime-methyl

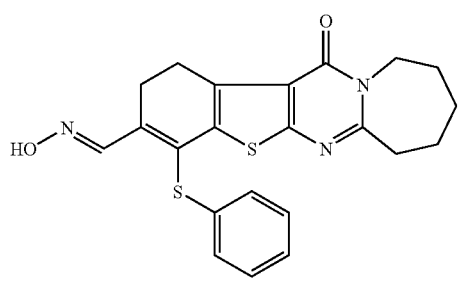

$^1$H NMR δ 1.81 (6H, m), 2.96 (4H, m), 3.30 (2H, m), 4.34 (2H, m), 7.18 (5H, m), 7.61 (1H, broad s), 8.76 (1H, s). M/z 423

EXAMPLE 3

Scheme 3. Synthesis of compound 8

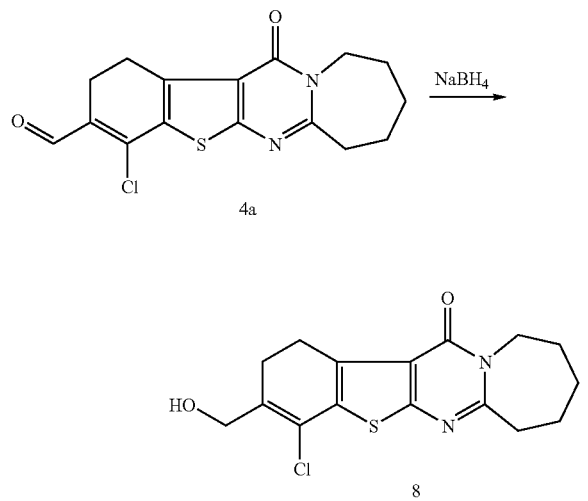

8  4-Chloro-1,2,7,8,9,10,11,13-octahydro-13-oxo[1]benzothieno[2',3':4,5]-pyrimido[1,2-a]azepine-3-hydroxymethyl $^1$H NMR δ 1.84 (6H, m), 2.71 (2H, m), 3.05 (2H, m), 3.25 (2H, m), 4.36 (2H, m), 4.45 (2H, s).

M/z 366

EXAMPLE 4

Scheme 4. Synthesis of compound 9

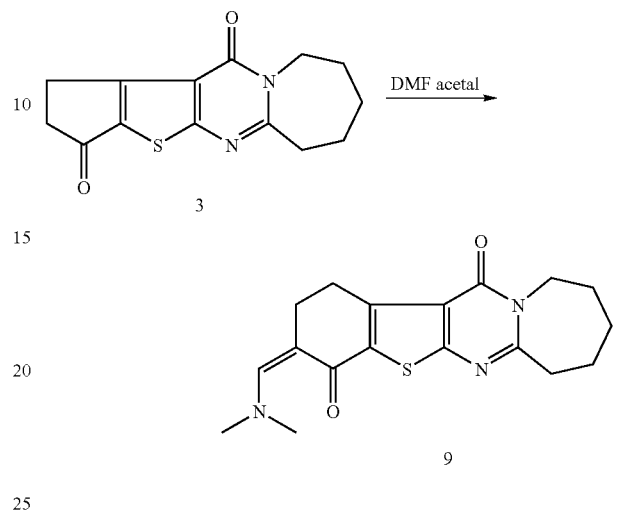

Synthesis of 9: Dry DMF (5 ml), DMF acetal (1.56 mmol) and 3b (0.36 mmol) were refluxed for 2 hours under a CaCl₂-tube, after which DMF was distilled away and the crude product dried in a vacuum. Purification in a flash column using acetone as an eluent afforded 9 in 55% yield. $^1$H NMR (CDCl₃) δ 1.86 (6H, m), 3.08 (2H, m), 3.17 (6H, s), 4.08 (2H, s), 4.40 (2H, m), 7.41 (1H, s).

EXAMPLE 5

Scheme 5. Synthesis of compound 10

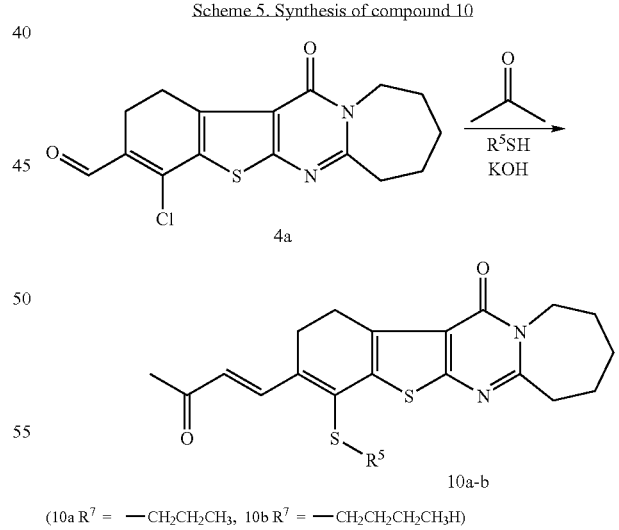

(10a R⁷ = —CH₂CH₂CH₃, 10b R⁷ = —CH₂CH₂CH₂CH₃)

General procedure for the synthesis of 10a-10b: KOH (0.58 mmol) and EtSH (0.59 mmol) in EtOH (5 ml) were stirred for 30 minutes, followed by addition of 4a in acetone (40 ml). After 30 minutes water (250 ml) was added and the mixture stirred until the product precipitates. Filtration afforded 10a as yellow powder in 86% yield.

10a 1,2,7,8,9,10,11,13-Octahydro-13-oxo-4-(propylthio)[1]benzothieno[2',3':4,5]-pyrimido-[1,2-a]azepine-3-(3-oxo)but-1-ene

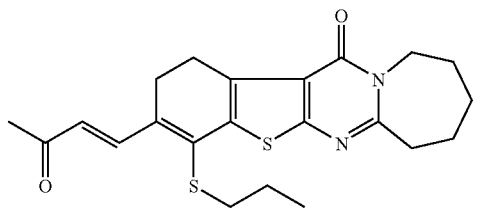

¹H NMR (CDCl₃) δ 1.00 (3H, t), 1.60 (2H, m), 1.85 (6H, m), 2.39 (3H, s), 2.75 (4H, m), 3.05 (2H, m), 3.27 (2H, m), 4.37 (2H, m), 6.35 (1H, d), 8.28 (1H, d)

10b 1,2,7,8,9,10,11,13-Octahydro-13-oxo-4-(butylthio)[1]benzothieno[2',3':4,5]-pyrimido-[1,2-a]azepine-3-(3-oxo)but-1-ene

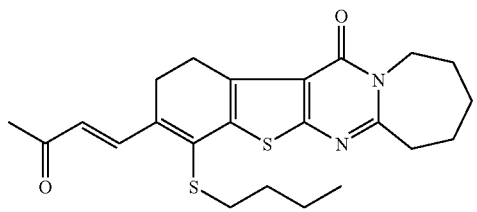

¹H NMR (CDCl₃) δ 0.88 (3H, t), 1.46 (4H, m), 1.85 (6H, m), 2.38 (3H, s), 2.76 (4H, m), 3.05 (2H, m), 3.27 (2H, m), 4.37 (2H, m), 6.35 (1H, d), 8.27 (1H, d)

FURTHER EXAMPLES 12 7,8,9,10,11,13-Hexahydro-13-oxo-4-(phenylthio)-[1]benzothieno[2',3':4,5]pyrimido[1,2-a]azepine-3-carbaldehyde

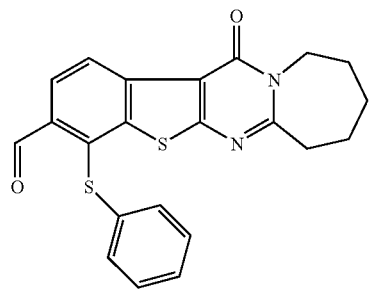

Compound 5a (100 mg, 245 mmol) and DDQ (67 mg, 295 mmol) were refluxed over night in 15 ml of dry benzene. The reaction mixture was cooled to room temperature and filtered through a short column of silica gel. The solvent was evaporated. The product 12 was recrystallized from EtOH/petrol ether.

¹H NMR (CDCl₃) δ 1.86 (6H, m), 3.12 (2H, m), 4.47 (2H, m), 7.16 (5H, m), 8.16 (1H, d), 8.72 (1H, d), 10.78 (1H, s)

13 1,2,3,4,7,8,9,10,11,12-Decahydro-4-hydroxy-14H-[1]benzothieno[2',3':4,5]pyrimido[1,2-a]azocin-14-one

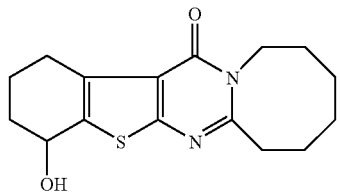

To compound 3d (200 mg, 0.66 mmol) in 5 ml of THF and 15 ml of EtOH, NaBH₄ (33 mg, 0.86 mmol) was added and the reaction mixture was stirred for 15 minutes. The reaction was quenched with water and extracted with CH₂Cl₂. The organic layer was washed with brine and dried with Na₂SO₂. After filtration the solvent was evaporated. The product was purified by flash chromatography using CH₂Cl₂/EtOAc 1:1 as an eluent.

¹H NMR (CDCl₃) δ 1.42 (2H, m), 1.59 (2H, m), 1.95 (7H, m), 2.14 (2H, m), 3.05 (4H, m), 4.29 (2H, m), 4.87 (1H, m)

14 9-Methyl-2,3,4,7,8,9,10,11-octahydro-[1]benzothieno[2',3':4,5]pyrimido[1,2-a]azepin-13(1H)-one

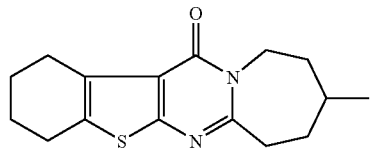

The compound was synthesized by the method described for 2a-i using 4-methyl-caprolactam as a starting material.

¹H NMR δ 0.98 (3H, d), 1.26 (2H, m), 1.84 (5H, m), 2.04 (2H, m), 2.74 (2H, m), 3.01 (4H, m), 3.51 (1H, m), 5.17 (1H, m)

MS (m/z) 288

15 1,2,3,4,7,9,10,12-Octahydro-12-oxo-8H-[1]benzothieno[2,3-d]pyrido[1,2-a]pyrimidine-7-carboxylic acid ethyl ester

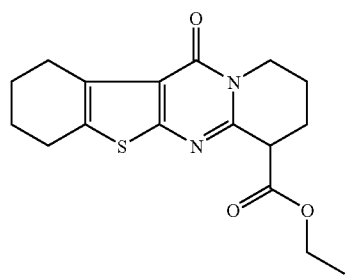

The compound was synthesized by the method described for 2a-i using 3-ethoxy-carbonyl-2-piperidone as a starting material.

¹H NMR δ 1.24 (3H, t), 1.99 (7H, m), 2.27 (1H, m), 2.74 (2H, m), 2.99 (2H, m), 4.01 (3H, m), 4.20 (2H, q)

MS (m/z) 332

16    1,2,3,4,7,8,9,10,11,13-Decahydro-13-oxo-[1]benzothieno[2',3':4,5]pyrimido[1,2-a]azepine-9-carboxylic acid ethyl ester

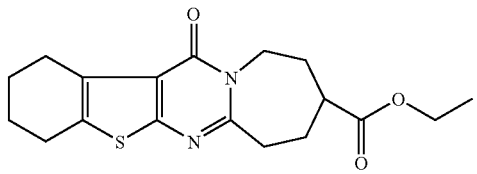

The compound was synthesized by the method described for 2a-i using ethyl 7-oxo-4-azepanecarboxylate as a starting material.

$^1$H NMR δ 1.23 (3H, t), 1.88 (6H, m), 2.15 (2H, m), 2.72 (3H, m), 3.03 (4H, m), 3.91 (1H, m), 4.13 (2H, q), 4.84 (1H, m)

17    2,3,8,9,10,11-Hexahydro-9-methyl-[1]benzothieno[2',3':4,5]pyrimido[1,2-a]azepine-4,13(1H,7H)-dione

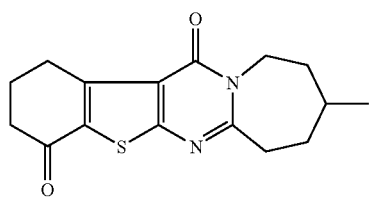

To compound 14 (4.0 g, 13.9 mmol), potassium peroxodisulfate (11.3 g, 41.6 mmol) and CuSO$_4$.5H$_2$O, 250 ml of acetinitrile/water 1:1 were added. The reaction mixture was heated to reflux for 30 minutes. The reaction was quenched with water and extracted with CH$_2$Cl$_2$. The organic layer was washed with 10% sodium thiosulfate and brine, and dried over Na$_2$SO$_4$. After filtration the solvent w as evaporated and the product purified by flash chromatography using CH$_2$Cl$_2$/EtOAc 9:1 as an eluent.

$^1$H NMR (CDCl$_3$) δ 1.00 (3H, d), 1.28 (2H, m), 1.90 (1H, m), 2.08 (2H, m), 2.23 (2H, m), 2.66 (2H, m), 3.06 (2H, m), 3.28 (2H, m), 3.55 (1H, m), 5.16 (1H, m)

MS (m/z) 302

18    4,12-Dioxo-1,2,3,4,7,9,10,12-octahydro-8H-[1]benzothieno[2,3-d]pyrido[1,2-a]pyrimidine-7-carboxylic acid ethyl ester

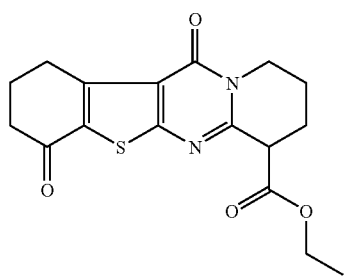

Compound 18 was synthesized by the method described for compound 17 using compound 15 as a starting material.

$^1$H NMR (CDCl$_3$) δ 1.26 (3H, t), 1.80 (1H, m), 2.18 (4H, m), 2.62 (3H, m), 3.24 (3H, m), 3.81 (1H, m), 4.28 (3H, m)

19    4,13-Dioxo-1,2,3,4,7,8,9,10,11,13-decahydro-[1]benzothieno[2',3': 4,5]pyrimido[1,2-a]azepine-9-carboxylic acid ethyl ester

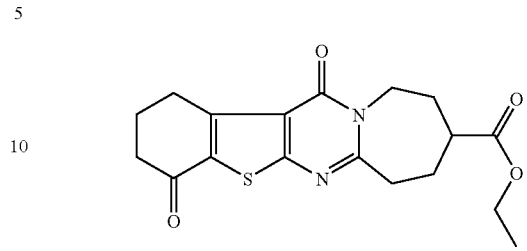

Compound 19 was synthesized by the method described for compound 17 using compound 16 as a starting material.

$^1$H NMR (CDCl$_3$) δ 1.28 (3H, t), 1.97 (2H, m), 2.21 (4H, m), 2.66 (2H, m), 2.79 (1H, m), 3.03 (1H, m), 3.24 (3H, m), 4.01 (1H, m), 4.18 (2H, q), 4.84 (1H, m)

20    4-Chloro-9-methyl-1,2,7,8,9,10,11,13-octahydro-13-oxo-[1]benzothieno[2',3': 4,5]pyrimido [1,2-a]azepine-3-carbaldehyde

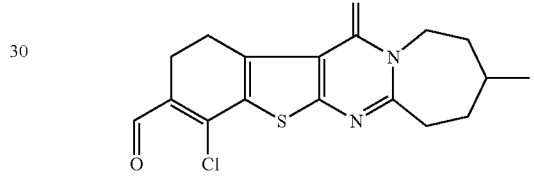

POCl$_3$ (2.91 mmol) was added dropwise into DMF (3.02 mmol) in CHCl$_3$ (2 ml) at 0° C. After 30 minutes compound 17 (0.36 mmol) in CHCl$_3$ (6 ml) was added slowly dropwise. The reaction mixture was allowed to reach room temperature and stirred overnight after which the reaction mixture was heated to 50° C. for 12 hours. The reaction mixture was cooled to room temperature and quenched with saturated NaOAc, extracted with CH$_2$Cl$_2$, washed with brine and water, and dried over Na$_2$SO$_4$. After filtration the solvent was evaporated. The product was purified by flash chromatography using CH$_2$Cl$_2$-EtOAc 9:1 as an eluent.

$^1$H NMR (CDCl$_3$) δ 1.00 (3H, d), 1.29 (2H, m), 1.90 (1H, m), 2.09 (2H, m), 2.80 (2H, m), 3.06 (2H, m), 3.27 (2H, m), 3.55 (1H, m), 5.15 (1H, m), 10.20 (1H, s)

21    4-Chloro-3-formyl-1,2,7,8,9,10,11,13-octahydro-13-oxo-[1]benzothieno[2',3': 4,5]pyrimido[1,2-a]azepine-9-carboxylic acid ethyl ester

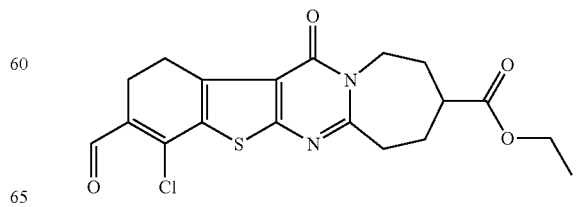

Compound 21 was synthesized by the method described for 4a using compound 19 as a starting material, with the exception that the reaction mixture was stirred for 8 days.

¹H NMR (CDCl₃) δ 1.28 (3H, t) 1.98 (2H, m), 2.22 (2H, m), 2.79 (3H, m), 3.03 (1H, m), 3.24 (3H, m), 4.01 (1H, m), 4.18 (2H, q), 4.85 (1H, m), 10.20 (1H, s)

22 3-Formyl-1,2,7,8,9,10, 11,13-octahydro-13-oxo-4-(propylthio)-[1]benzothieno [2',3': 4,5]pyrimido[1,2-a]azepine-9-carboxylic acid ethyl ester

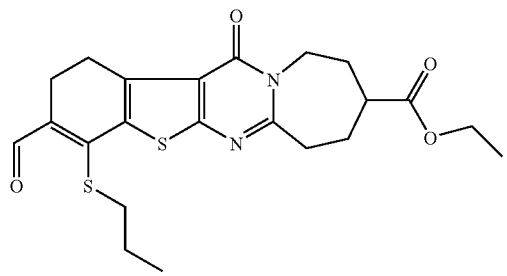

Compound 22 was synthesized by the method described for 5c using compound 21 as a starting material.

¹H NMR (CDCl₃) δ 0.99 (3H, t), 1.27 (3H, t), 1.62 (2H, m), 1.97 (2H, m), 2.22 (2H, m), 2.77 (3H, m), 2.86 (2H, t), 3.02 (1H, m), 3.21 (3H, m), 4.00 (1H, m), 4.17 (2H, q), 4.86 (1H, m), 10.49 (1H, s)

23 3-Formyl-1,2,7,8,9,10,11,13-octahydro-13-oxo-4-(propylthio)-[l]benzothieno[2',3': 4,5] pyrimido[1,2-a]azepine-9-carboxylic acid methyl ester

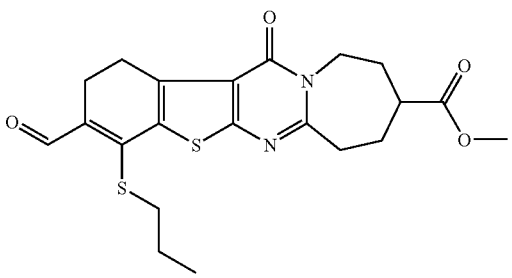

Compound 22 80.37 mmol) was dissolved into MeOH (10 ml), and KOH (0.98 mmol) in MeOH (5 ml) was added. The reaction mixture was stirred for 2 hours in room temperature. The reaction mixture was poured into water, acidified with HCl and extracted with CH₂Cl₂. Organic layer was washed with brine and dried with Na₂SO₄. After filtration the solvent was evaporated. Purification by flash chromatography using CH₂Cl₂-EtOAc 9:1 as an eluent afforded compound 23 as a major product and compound 24 as a minor product.

23 ¹H NMR (CDCl₃) δ 0.99 (3H, t), 1.63 (2H, m), 1.98 (2H, m), 2.23 (2H, m), 2.77 (3H, m), 2.86 (2H, t), 3.02 (1H, m), 3.21 (3H, m), 3.73 (3H, s), 4.01 (1H, m), 4.84 (1H, m), 10.49 (1H, s)

24 3-Formyl-4-methoxy-1,2,7,8,9,10,11,13-octahydro-13-oxo-[1]benzothieno[2',3': 4,5]pyrimido [1,2-a]azepine-9-carboxylic acid methyl ester

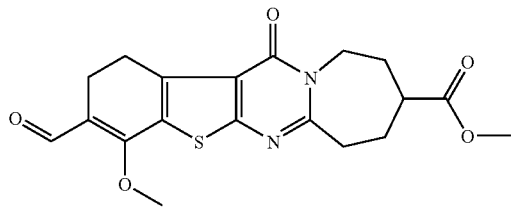

¹H NMR (CDCl₃) 1.98 (2H, m), 2.20 (2H, m), 2.72 (2H, m), 2.80 (1H, m), 3.02 (1H, m), 3.21 (3H, m), 3.73 (3H, s), 4.04 (3H, s), 4.04 (1H, m), 4.84 (1H, m), 10.19 (1H, s)

25 1,2,3,4-Tetrahydro-12H-[1]benzothieno[2,3-d]pyrido[1,2-a]pyrimidin-12-one

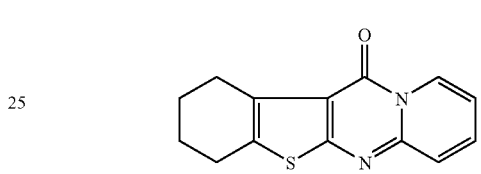

2-Bromopyridine and ethyl 2-amino-4,5,6,7-tetrahydrobenzo(b)thiophene-3-carboxylate 1b were heated to 165° C. for three and half hours under argon. After cooling the solid material was crystallized from EtOH. The crystallised product was purified by flash chromatography using CH₂Cl₂/EtOAc 9:1 as an eluent.

¹H NMR (CDCl₃) δ 1.92 (4H, m), 2.81 (2H, m), 3.14 (2H, m), 7.00 (1H, m), 7.57 (2H, m), 9.04 (1H, m)
MS (m/z) 256

26 2,3-Dihydro-12H-[l]benzothieno[2,3-d]pyrido[1,2-a]pyrimidin-4, 12(1H)-dione

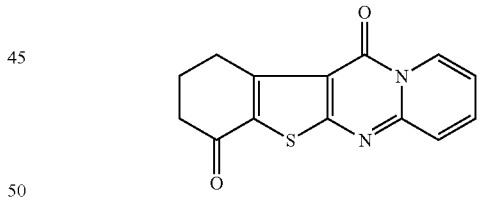

Compound 26 was synthesized by the method described for compound 17 using compound 25 as a starting material.

¹H NMR (CDCl₃) δ 2.30 (2H, m) 2.71 (2H, m), 3.40 (2H, t), 7.12 (1H, m), 7.62 (1H, m), 7.76 (1H, m), 9.05 (1H, m)

27 3-Methyl-2,3,4,7,8,9, 10,11-octahydro-[1]benzothieno [2',3': 4,5]pyrimido-[1,2-a]azepin-13(1H)-one

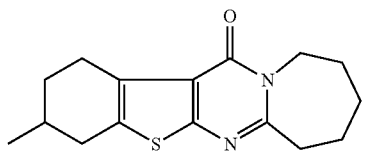

Compound 27 was synthesized by the method described for 2a-i using 2-amino-4,5,6,7-tetrahydro-6-methyl-benzo[b]thiophene-3-carboxylic acid ethyl ester as a starting material.

$^1$H NMR (CDCl$_3$) δ 1.09 (3H, d), 1.44 (1H, m), 1.89 (8H, m), 2.37 (1H, m), 2.85 (2H, m), 3.02 (2H, m), 3.21 (1H, m), 4.35 (2H, m)

MS (m/z) 288

28 2,3,8,9,10,11-Hexahydro-3-methyl-[1]benzothieno[2',3': 4,5]pyrimido[1,2-a]azepin-4,13(1H,7H)-dione

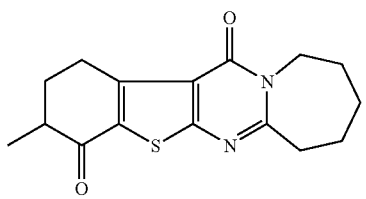

Compound 28 was synthesized by the method described for compound 17 using compound 27 as a starting material.

$^1$H NMR (CDCl$_3$) δ 1.28 (3H, d), 1.85 (6H, m), 1.98 (1H, m), 2.29 (1H, m), 2.67 (1H, m), 3.06 (2H, m), 3.13 (1H, m), 3.50 (1H, m), 4.36 (2H, m)

29 3-t-Butyl-2,3,4,7,8,9,10,11-octahydro-[1]benzothieno[2',3': 4,5]pyrimido-[1,2-a]azepin-13(1H)-one

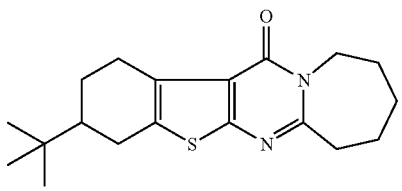

Compound 29 was synthesized by the method described for 2a-i using 2-amino-4,5,6,7-tetrahydro-6-t-butylbenzo[b]thiophene-3-carboxylic acid ethyl ester as a starting material.

$^1$H NMR (CDCl$_3$) δ 0.95 (9H, s), 1.35 (1H, m), 1.55 (1H, m), 1.79 (6H, m), 2.06 (1H, m), 2.51 (1H, m), 2.76 (2H, m), 3.01 (2H, broad s), 3.32 (1H, m), 4.35 (2H, m)

30 1,2,7,8,9,10,11,13-Octahydro-13-oxo-4-(phenylsulfinyl)-[1]benzothieno[2',3': 4,5]-pyrimido-[1,2-a]azepine-3-carbaldehyde

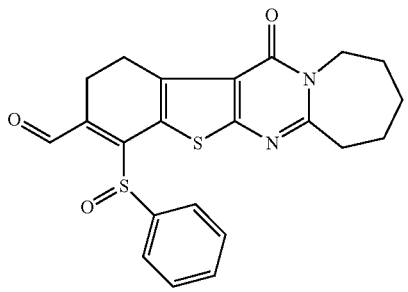

Compound 5a (100 mg, 0.25 mmol) and m-chloroperbenzoic acid (89 mg, 0.52 mmol) in 25 ml dry CH$_2$Cl$_2$ were stirred for 3 days in room temperature. The reaction was quenched with water and extracted with CH$_2$Cl$_2$. The organin layer was washed with 10% sodium thiosulfate and brine and dried with Na$_2$SO$_4$. After filtration the solvent was evaporated and the product purified by flash chromatography using CH$_2$Cl$_2$/EtOAc 8:2

$^1$H NMR (CDCl$_3$) δ 1.80 (6H, m), 2.71 (2H, m), 3.03 (2H, m), 3.06 (1H, m), 3.57 (1H, m), 4.31 (2H, m), 7.47 (3H, m), 7.69 (2H, m), 10.65 (1H, s)

31 4-Chloro-1,2,7,8,9, 10,11,13-octahydro-13-oxo-[1]benzothieno[2',3': 4,5]pyrimido[1,2-a]azepine-3-carboxylic acid

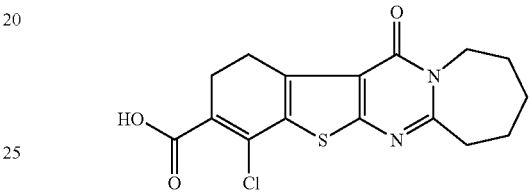

Compound 4a (335 mg, 1.00 mmol) and 2-methyl-2-butene (1.06 ml, 10.01 mmol) were dissolved into 50 ml THF. A freshly prepared solution of 80% NaClO$_2$ (339 mg, 3.00 mmol) and NaH$_2$PO$_4$.H$_2$O (414 mg, 3.00 mmol) in 55 ml of t-BuOH/H$_2$O 5:1 was added. The reaction mixture was stirred in room temperature for 6 hours. The reaction was quenched with water and extracted CH$_2$Cl$_2$. The organic phase was extracted with sat. NaHSO$_4$. The water phase was then made acidic with HCl and extracted with CH$_2$Cl$_2$. the organic layer was washed with brine and dried over Na$_2$SO$_2$. After filtration the solvent was evaporated ant the product recrystallized from ethanol.

$^1$H NMR (D$_6$-DMSO) 1.71 (6H, m), 2.79 (2H, m), 3.06 (2H, m), 3.14 (2H, m), 4.31 (2H, m), 13.07 (1H, broad s)

32 4-Hydroxy-3-methyl-2,3,4,7,8,9,10,1-octahydro [1]benzothieno[2',3': 4,5]pyrimido-[1,2-a]azepin-13(1H)-one

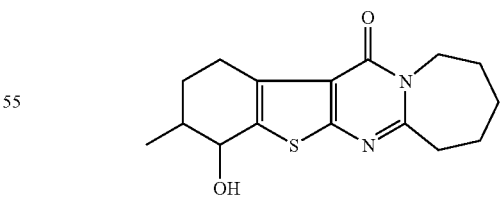

Compound 32 was synthesized as mixture of diastereomers by the method described for compound 13 using compound 28 as a starting material.

$^1$H NMR (CDCl$_3$) δ 1.14 (2H, d) 1.16 (2H, d), 1.58-2.04 (20H, m), 2.82 (1H, m), 2.95 (1H, m), 3.04 (4H, m), 3.13 (1H, m), 3.25 (1H, m), 3.75 (2H, m), 4.35 (4H, m), 4.42 (1H, m), 4.67 (1H, m)

33  3-Formyl-1,2,7,8,9,10,11,13-octahydro-13-oxo-4-(propylthio)-[1]benzothieno[2',3': 4,5] pyrimido[1,2-a]azepine-9-carboxylic acid

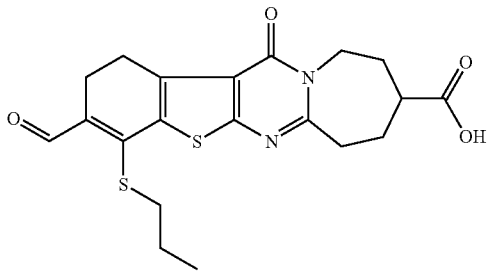

Compound 22 (130 mg) in THF (2 ml) and 0.7 ml 10% KOH H$_2$O/MeOH (2:1) were stirred over night in room temperature. The reaction mixture was poured into water and washed with ether. The water phase was acidified with HCl and extracted with EtOAc. Organic phase was washed with brine and dried with Na$_2$SO$_4$. After filtration the solvent was evaporated and the product recrystallized from ethanol.

$^1$H NMR (D$_6$-DMSO) δ 0.93 (2H, t), 1.55 (2H, m), 1.71 (2H, m), 2.14 (2H, m), 2.65 (2H, t), 2.67 (2H, m), 2.91 (2H, m), 3.10 (2H, m), 3.12 (2H, m), 3.97 (1H, m), 4.74 (1H, m), 10.36 (1H, s), 12.37 (1H, broad s); MS (m/z) 418

34  9-Methyl-1,2,7,8,9,10,11,13-octahydro-13-oxo-4-(propylthio)-[1]benzothieno[2',3': 4,5]-pyrimido[1,2-a]azepine-3-carbaldehyde

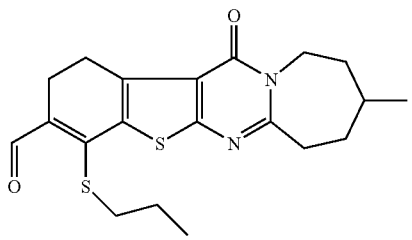

Compound 34 was synthesized by the method described for 5c using compound 21 as a starting material.

$^1$H NMR (CDCl$_3$) δ 0.99 (3H, t), 1.00 (3H, d), 1.28 (2H, m), 1.63 (2H, m), 1.89 (1H, m), 2.08 (2H, m), 2.75 (2H, m), 2.86 (2H, t), 3.06 (2H, m), 3.21 (2H, m), 3.55 (1H, m), 5.16 (1H, m), 10.49 (1H, s)

35  9-(Hydroxymethyl)-2,3,4,7,8,9,10,11-octahydro-[1]benzothieno[2',3': 4,5]pyrimido[1,2-a]azepin-13(1H)-one

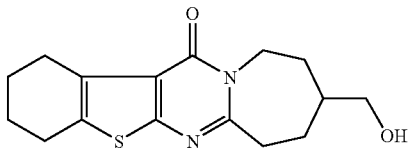

Compound 16 (0.72 mmol) in dry THF (6 ml) was added dropwise to LiAlH$_4$ (1.95 mmol) in THF (2 ml) under argon at 0° C. The reaction mixture was stirred for 20 minutes. The reaction was quenched with water and 10% NaOH was added, and extracted with ether. The organic layer was washed with brine and dried over Na$_2$SO$_4$. After filtration the solvent was evaporated and the product purified by flash chromatography using EtOAc as an eluent.

$^1$H NMR (CDCl$_3$) δ 1.31 (2H, m), 1.80 (6H, m), 2.18 (2H, m), 2.75 (2H, m), 3.01 (3H, m), 3.11 (1H, m), 3.51 (3H, m), 5.25 (1H, m)

It is evident that otherwise ring-substituted or -modified compounds as defined by formula (I) of the claims can be prepared analogously, e.g. by using ring-substituted or -modified analogues of the starting compound (2) in Scheme 2.

Further compounds of general formula IV falling under the scope of general formula I can prepared by parallel chemistry using a reaction as shown in the following scheme 6:

Scheme 6:
General procedure for the pyrimidinone synthesis of thiophene amino ester with lactames.

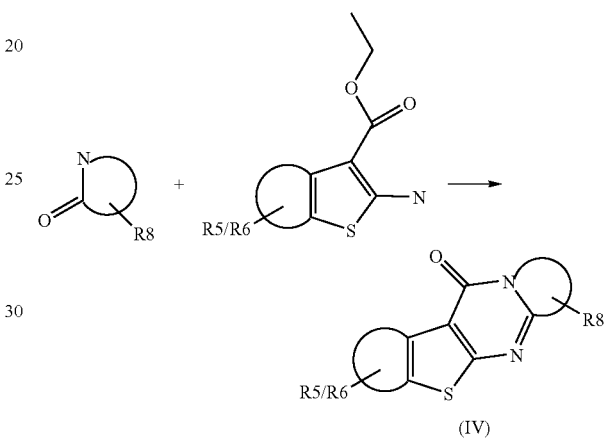

In a reaction vessel at room temperature are put together sequentially 0.25 M lactam, 0.25 M amino ester and 0.25 M POCl$_3$. Of all reactants one equivalent is used as solution or suspension in chlorobenzene. After shaking for 80 hours at 100° C., the mixtures are cooled to room temperature, washed with 5% NaOAc and extracted with EtOAc. The organic layers are collected and concentrated to yield the desired compound. The obtained material of the formula IV was thereafter analyzed by LC-MS.

The LC-MS system consists of 2 Perkin Elmer series 200 micro-pumps. The pumps are connected to each other by a 50 μl tee mixer. The mixer is connected to the Gilson 215 autosampler.

The LC method consists of the following steps:

| Step | total time | flow (ul/min) | A(%) | B(%) |
| --- | --- | --- | --- | --- |
| 0 | 0 | 2300 | 95 | 5 |
| 1 | 1.8 | 2300 | 0 | 100 |
| 2 | 2.5 | 2300 | 0 | 100 |
| 3 | 2.7 | 2300 | 95 | 5 |
| 4 | 3.0 | 2300 | 95 | 5 |

Solution A=100% Water with 0.025% HCOOH and 10 mmol NH$_4$HCOO pH=+/−3
Solution B=100% MeOH with 0.025% HCOOH The auto sampler has a 2 μl injection loop. The auto sampler is connected to a Varian Polaris C18 A 30*4.6 mm column with 3 μm particles. The column is thermo stated in a Perkin Elmer series 200 column oven at 40° C. The column is connected to an Applied Biosystems ABI 785 UV meter with a 2.7 μl flowcel. The wavelength is set to 254 nm. The UV meter is connected to a Sciex API 150EX mass spectrometer having the following parameters (Scanrange:150-900 Amu, Polarity: positive, Scan mode: profile, Resolution Q1: UNIT, Step size: 0.10 amu, Time per scan: 0.500 sec, NEB: 10, CUR: 10, IS: 5200, TEM: 325, DF: 30, FP: 225, EP: 10). The light scattering detector is connected to the Sciex API 150. The light scattering detector is a Sedere Sedex 55 operating at 50° C. and 3 bar $N_2$ pressure. The complete systems is controlled by a Dell optiplex GX400 computer operating under Windows NT.

The following table 4 lists compounds No. 41 to 53 of the general formula IV, which were prepared according to Scheme 6 starting with the lactams and the amino acid esters. In addition, the Molecular Weight and the Retention Time of the synthesized compounds determined by the LC-MS analysis are shown.

TABLE 4

Compounds No. 41 to 53 of the general formula IV:

| No. | Structural Formula | Amino ester | Lactam | MH+ | RT |
|---|---|---|---|---|---|
| 40 | | ETHYL 2-AMINO-4,5,6,7-TETRA-HYDROBENZO[B]THIO-PHENE-3-CARBOX-LATE | 2-AZA-CYCLOOCTANONE | 288.13 | 1.915 |
| 41 | | ETHYL 2-AMINO-BEN-ZO[B]THIOPHENE-3-CARBOXY-LATE | 2-AZA-CYCLOOCTA-NONE | 284.10 | 1.897 |
| 42 | | 2-AMINO-7-HYDROXY-BEN-ZO[B]THIOPHENE-3-CAR-BOXYLIC ACID ETHYL ESTER | 2-AZA-CYCLOOCTA-NONE | 300.09 | 1.700 |
| 43 | | ETHYL 2-AMINO-7-OXO-4,5,6,7-TETRA-HYDRO-1-BENZO-THIOPHENE-3-CARBOXY-LATE | 2-AZA-CYCLOOCTA-NONE | 302.11 | 1.684 |
| 44 | | ETHYL 2-AMINO-BEN-ZO[B]THIOPHENE-3-CARBOXY-LATE | DELTA-VALERO-LACTAM | 256.07 | 1.736 |
| 45 | | ETHYL 2-AMINO-BEN-ZO[B]THIOPHENE-3-CARBOXY-LATE | 3-CARBETHOXY-2-PIPERIDONE | 328.09 | 2.039 |
| 46 | | ETHYL 2-AMINO-BEN-ZO[B]THIOPHENE-3-CARBOXY-LATE | EPSILON-CAP-ROLACTAM | 270.08 | 1.858 |

TABLE 4-continued

Compounds No. 41 to 53 of the general formula IV:

| No. | Structural Formula | Amino ester | Lactam | MH+ | RT |
|---|---|---|---|---|---|
| 47 | | 2-AMINO-7-HYDROXY-BENZO[B]THIOPHENE-3-CARBOXYLIC ACID ETHYL ESTER | EPSILON-CAPROLACTAM | 286.08 | 1.645 |
| 48 | | ETHYL 2-AMINO-BENZO[B]THIOPHENE-3-CARBOXYLATE | N-ETHYL-2,3-DIKETOPIPERAZINE | 299.07 | 1.509 |
| 49 | | 2-AMINO-7-HYDROXY-BENZO[B]THIOPHENE-3-CARBOXYLIC ACID ETHYL ESTER | N-ETHYL-2,3-DIKETOPIPERAZINE | 315.07 | 1.386 |
| 50 | | ETHYL 2-AMINO-4,5,6,7-TETRAHYDROBENZO[B]THIOPHENE-3-CARBOXYLATE | N-ETHYL-2,3-DIKETOPIPERAZINE | 303.10 | 1.576 |
| 51 | | ETHYL 2-AMINO-7-OXO-4,5,6,7-TETRAHYDRO-1-BENZOTHIOPHENE-3-CARBOXYLATE | N-ETHYL-2,3-DIKETOPIPERAZINE | 317.08 | 1.277 |
| 52 | | ETHYL 2-AMINO-BENZO[B]THIOPHENE-3-CARBOXYLATE | 4-METHOXY-3-PYRROLIN-2-ONE | 270.05 | 1.703 |
| 53 | | ETHYL 2-AMINO-4,5,6,7-TETRAHYDROBENZO[B]THIOPHENE-3-CARBOXYLATE | 4-METHOXY-3-PYRROLIN-2-ONE | 274.08 | 1.782 |

Biological Testing Materials and Methods

1. Inhibition of the 17β-hydroxysteroid dehydrogenase type 1, type 2 and type 3 enzyme The compounds were screened in respect of 17β-HSD enzyme activity in vitro on established M CF-7 cell lines, each stably expressing one of the respective 17β-HSD isoenzymes. The interconversion of substrate by each isoenzyme and the 17β-HSD inhibiting activity of chemical compounds in these cell lines were detected by HPLC system.

Varying amounts of the test compounds were incubated in the growth medium of the 17β-HSD expressing cells together tritium labeled substrate (2 nM estrone for 17β-HSD type 1; 2 nM estradiol for 17β-HSD type 2; and 2 nM androstenedione for 17β-HSD type 3). The medium samples were removed after exact incubation time and the reaction is stopped by trichloroacetic acid (TCA). The samples were analyzed by HPLC-coupled flow scintillation analysis.

For each enzyme type, the HSD-inhibiting activity of an individual test compound was calculated by comparing the conversion of a control sample without any test compound (referred to as "Negative Control") to the (reduced) conversion of the test sample containing the particular compound to be tested (referred to as "Test Sample").

$$\% \text{ inhibition} = 100 \times \frac{\text{Conversion in Negative Control} - \text{Conversion in Test Sample}}{\text{Conversion Negative Control}}$$

The obtained results are shown in Table 3 below. Two concentrations of each compound were used. The number of the compound refers to the numbers indicated in the Experimental Section.

TABLE 3

% Inhibition of the 17β-HSD enzymes type 1, type 2 and type 3 by the compounds of the invention

| Compound | HSD1 | | HSD2 | | HSD3 | |
|---|---|---|---|---|---|---|
| | 1 μM | 10 μM | 1 μM | 10 μM | 1 μM | 10 μM |
| No. 2a | 10.0 | 45.9 | 16.2 | 23.4 | 39.0 | 24.9 |
| No. 2b | 21.0 | 15.0 | 15.9 | 21.4 | 4.2 | 9.5 |
| No. 2c | 22.7 | 39.8 | 8.9 | 13.5 | 50.8 | 47.0 |
| No. 2e | 15.8 | 20.0 | 26.0 | 28.9 | 46.8 | 38.8 |
| No. 2f | 19.9 | 19.2 | 37 | 32.4 | 48.2 | 40.4 |
| No. 2g | 30.7 | 37.0 | 44.9 | 24.9 | 51.7 | 51.3 |
| No. 2i | 12.7 | 18.5 | 20.6 | 29.4 | 4.4 | 9.9 |
| No. 3b | 13.5 | 20.7 | 14.1 | 25.4 | 0.3 | 13.7 |
| No. 3d | 14.3/18.2[x)] | 42.9/37.6[x)] | 14.1 | 11.1 | 15.3/22.3[x)] | 16.7/8.1[x)] |
| No. 3e | 6.3 | 35.8 | 25.7 | 16.3 | 38.5 | 47.4 |
| No. 3f | 8.7 | 22.0 | 31.1 | 21.8 | 43.9 | 40.2 |
| No. 4a | 27.9 | 78.0 | 7.7 | 22.5 | 9.4 | 53.8 |
| No. 4b | 36.9/31.2[x)] | 82.1/80.1[x)] | 3.5 | 1.5 | 5.3/14.3[x)] | 42.1/43.9[x)] |
| No. 4e | 23.5/24.6[x)] | 44.4/52.1[x)] | 9.6 | 28.3 | 9.8/11.1[x)] | 14.2/17.3[x)] |
| No. 5b | 66.1 | 100.0 | 19.7 | 25.2 | 43.4 | 100.0 |
| No. 5c | 74.0 | 100.0 | 8.9 | 18.6 | 10.5 | 100.0 |
| No. 5d | 54.1 | 100.0 | 8.2 | 15.1 | 32.6 | 72.0 |
| No. 5e | 71.9 | 100.0 | 8.4 | 20.2 | 50.8 | 86.3 |
| No. 5i | 43.9 | 100.0 | 11.6 | 17.3 | 22.5 | 80.5 |
| No. 6a | 51.8 | 100.0 | 11.6 | 42.5 | 45.9 | 48.9 |
| No. 6c | 47.7 | 82.4 | 37.5 | 36.7 | 20.4 | 38.1 |
| No. 11 | 4.7 | 51.1 | 16.7 | 28.3 | 7.3 | 31.7 |
| No. 12 | 15.1 | 87.9 | 7.0 | 8.9 | 8.6 | 25.5 |
| No. 13 | 5.0 | 20.0 | 1.7 | 18.6 | −2.2 | 11.7 |
| No. 14 | 12.8 | 19.6 | 5.9 | 14.9 | 27.6 | 34.2 |
| No. 15 | 14.8 | 24.5 | 10.7 | 15.7 | −0.3 | 13.5 |
| No. 16 | 17.2 | 18.6 | 3.0 | 24.8 | 13.6 | 22.9 |
| No. 17 | 18.4 | 39.4 | 15.2 | 20.1 | 21.6 | 32.4 |
| No. 18 | 0.5 | 9.5 | 18.7 | 23.8 | −3.0 | 21.3 |
| No. 19 | 10.6 | 33.1 | 0.6 | 4.4 | 13.0 | 10.5 |
| No. 20 | 10.4 | 45.7 | 11.2 | 6.2 | 32.0 | 100.0 |
| No. 21 | 10.9 | 33.5 | 13.1 | 32.9 | 20.0 | 87.3 |
| No. 22 | 24.3 | 46.5 | 6.8 | 16.1 | 25.5 | 100.0 |
| No. 23 | 17.4 | 64.7 | 9.7 | 17.7 | 19.5 | 89.5 |
| No. 24 | 24.9 | 32.3 | 3.1 | 19.3 | 18.0 | 59.6 |
| No. 25 | 6.2 | 8.7 | 14.0 | 33.6 | −3.2 | 7.9 |
| No. 26 | 6.4 | −0.8 | 15.1 | 16.4 | −2.1 | 0.3 |
| No. 27 | 11.4 | 25.6 | 5.3 | 3.2 | 22.9 | 24.9 |
| No. 28 | 14.3 | 15.3 | 18.2 | 18.7 | 7.8 | 9.5 |
| No. 29 | −1.0 | 1.3 | 13.1 | 10.1 | 14.9 | 25.8 |
| No. 30 | 23.1 | 49.0 | 12.8 | 24.8 | 11.1 | 31.2 |
| No. 31 | 2.1 | 6.8 | −0.2 | 9.3 | −6.4 | −3.9 |
| No. 32 | 19.7 | 22.5 | 14.0 | −5.1 | n.d. | n.d. |
| No. 33 | 15.3 | 22.6 | 5.0 | −0.1 | n.d. | n.d. |
| No. 34 | 14.9 | 48.1 | 13.0 | −0.5 | n.d. | n.d. |
| No. 35 | 4.8 | 22.4 | 15.8 | 27.7 | 16.2 | 23.4 |

[x)]two tests were run

2. Estrogen Receptor Binding Assay The binding affinity of the compounds of the invention to the estrogen receptor α and to the estrogen receptor β may be determined according to the in vitro ER binding assays described by Koffmann et al. [Koffmann B et al. (1991) J. Steroid. Biochem. Mol. Biol. 38:135].

Alternatively, an estrogen receptor binding assay may be performed according to international patent application PCT/US/17799 (published as WO 00/07996).

3. Estrogen Receptor Transactivation Assays

Compounds of the invention showing binding affinity towards the estrogen receptor may be further tested with regard to their individual estrogenic or anti-estrogenic potential (agonistic binding or antagonistic binding to the ERα or ERβ). The determination of the estrogen receptor agonist activity may be performed according to an in vitro assay system using the MMTV-ERE-LUC reporter system which is for example described within U.S. patent application Ser. No. 10/289,079 (published as US 2003/0170292):

To assay estrogen receptor agonist activity, Hela cells are grown in 24-well microtiter plates and then transiently co-transfected with two plasmids using lipofectamine. The first plasmid comprises DNA encoding human estrogen receptor (either ER-alpha or ER-beta), and the second plasmid comprises an estrogen-driven reporter system comprising: a luciferase reporter gene (LUC) whose transcription is under the control of upstream regulatory elements comprising 4 copies of the vitellogenin estrogen response element (ERE) cloned into the mouse mammary tumor virus (MMTV) promoter (the full name for the reporter system being "MMTV-ERE-LUC"). Cells are exposed to the compounds of the invention in RPMI 1640 medium, supplemented with 10% charcoal-treated fetal calf serum, 2 mM L-glutamine, 0.1 mM non-essential amino acids and 1 mM sodium pyruvate for 42-48 hours at 37° C. in a 5% carbon dioxide incubator. Concurrently, cells exposed to estradiol (1 nM) serve as positive controls. Replicate wells exposed to the solvent in which the compounds of the invention are dissolved (i.e. ethanol or methanol) are used as negative controls. After the 42-48 hr incubation period, cells are rinsed with phosphate buffered saline (PBS), lysis buffer (Promega Corp) is added, and cell lysates are collected for measurement of luciferase activity with a luminometer. Estrogenic activity of the compounds of the invention is expressed as fold-increase in luciferase activity as compared to that observed in negative control cells.

Alternatively, the determination of the estrogen receptor transactivation activity (estrogenicity assay or agonist assay) and of the inhibitory potency of transactivation activity (anti-estrogenicity assay or antagonist assay) may be performed according to international patent application PCT/US/17799 (published as WO 00/07996).

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

CITED LITERATURE

The following documents provide background information and are hereby incorporated herein by reference.

Labrie et al. (2000) "Role of 17 beta-hydroxysteroid dehydrogenases in sex steroid formation in peripheral intracrine tissues" Trends Endocrinol Metab., 11:421-7

Labrie F et al. (1997) "The key role of 17 beta-hydroxysteroid dehydrogenases in sex steroid biology." Steroids, 62:148-58

Tamaya et al. (1985) "Comparison of cellular levels of steroid receptors in uterine leiomyoma and myometrium." Acta Obstet Gynecol Scand., 64:307-9

Poirier D. (2003) "Inhibitors of 17 beta-hydroxysteroid dehydrogenases" Curr Med Chem. 10:453-77

Geissler W M et al. (1994) "Male pseudohermaphroditism caused by mutations of testicular 17beta-hydroxysteroid dehydrogenase 3." Nat Genet., 7:34-9.

Oefelein M G & Cornum R (2000) "Failure to achieve castrate levels of testosterone during luteinizing hormone releasing hormone agonist therapy: the case for monitoring serum testosterone and a treatment decision algorithm." J Urol.; 164:726-9.

U.S. Pat. No. 6,541,463

WO 01/42181

WO 98/32724

WO 98/30556

WO 99/12540

Andersson S. (1995) "Molecular genetics of androgenic 17β-Hydroxysteroid Dehydrogenases". J. Steroid Biochem. Molec. Biol., [55:533-534].

Dong Y et al. (1998) "17β-hydroxysteroid dehydrogenases in human bone cells" J. Bone Min. Res., 13:1539-1546

WO 02/26706

DE2411273

Manhas M S, Sharma S D, A min S G. (1972) "Heterocyclic compounds. 4. Synthesis and antiinflammatory activity of some substituted thienopyrimidinones." J Med Chem. 15(1):106-7.

Kapustina M V; Kharizomenova I A; Shvedov V I; Radkevich T P; Shipilova L D (1992) "Synthesis and biological activity of 4,8-dioxo-3,4,5,6,7,8-hexahydrobenzothieno[2,3-d]pyrimidine derivatives" Khimiko-Farmatsevticheskii Zhurnal 26(1):56-7

Kapustina M V; Amelkin O Yu; Kharizomenova I A; Shvedov V I; Filitis L N (1991) "Synthesis and tuberculostatic activity of benzothieno[2,3-d]pyrimidines" Khimiko-Farmatsevticheskii Zhurnal 25(7): 38-9

Koffman B, Modarress K J, Beckerman T, Bashirelahi N. (1991) "Evidence for involvement of tyrosine in estradiol binding by rat uterus estrogen receptor." J Steroid Biochem Mol. Biol. 38(2): 135-9.

WO 00/07996

US 2003/0170292

What is claimed is:

1. A method of treating a steroid hormone dependent disease or disorder, requiring the inhibition of the 17β-HSD type 1, 17β-HSD type 2 or 17β-HSD type 3 enzyme, wherein the steroid hormone dependent disease or disorder is selected from the group consisting of breast cancer, prostate carcinoma, ovarian cancer, uterine cancer, colon cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, acne, hirsutism, androgenic alopecia, precocious puberty, adrenal hyperplasia, polycystic ovarian syndrome, urinary dysfunction and osteoporosis, said method comprising administering to a patient suffering from one or more of the aforementioned steroid hormone dependent diseases or disorders an effective amount of a compound corresponding to formula (I)

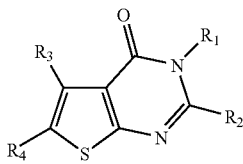

(I)

wherein
- $R_1$ and $R_2$ together with their binding sites form a cyclic 5-, 6-, 7- or 8-membered ring system, which is saturated or contains one or more double bonds between the ring atoms, and wherein said ring is optionally substituted with up to three substituents independently selected from the group consisting of alkyl, substituted alkyl, aryl or arylalkyl wherein the aryl group is optionally substituted, alkoxy, aryloxy, acyloxy, arylthio, alkylthio, aryl-$S(O)_{1-2}$—, alkyl-$S(O)_{1-2}$—, hydroxyl, oxo, halogen, amino, oxime, —(C=O)—R, —(C=O)—O—R, thiocarboxyl, and amido;
- $R_3$ and $R_4$ form together with their binding sites a cyclic 5-, 6-, 7- or 8-membered hydrocarbon ring system, which is saturated or contains one or more double bonds between the carbon atoms, and
- wherein said ring is optionally substituted with up to three substituents independently selected from the group consisting of alkyl, substituted alkyl, aryl or arylalkyl wherein the aryl group is optionally substituted, alkoxy, aryloxy, acyloxy, arylthio, alkylthio, aryl-$S(O)_{1-2}$—, alkyl-$S(O)_{1-2}$—, hydroxyl, oxo, halogen, amino, oxime, —(C=O)—R, —(C=O)—O—R, thiocarboxyl, and amido;
- wherein R may be hydrogen, alkyl, aryl, or aryl-($C_1$-$C_4$)-alkyl, both optionally substituted in the aryl group
or a physiologically acceptable salt thereof;
provided that said compound is not 1,2,7,8,9,10,11,13-octahydro-13-oxo-4-(phenylthio)-[1]benzothieno[2',3':4,5]pyrimido[1,2-a]azepine-3-carboxaldehyde.

2. A method according to claim 1, wherein said compound corresponds to formula (II)

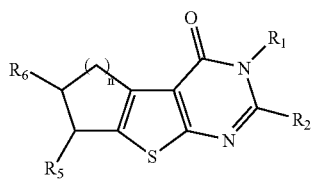

(II)

wherein
- $R_1$ and $R_2$ form together with their binding sites a cyclic 5-, 6-, 7- or 8-membered ring system,
which is saturated or contains one or more double bonds between the ring atoms, and
which ring contains zero, one or two N-atoms in addition to the nitrogen atom where $R_1$ is attached,
wherein said ring is substituted with zero, one or two substituents independently selected from the group consisting of alkyl, substituted alkyl, aryl, or arylalkyl, wherein the aryl group is optionally substituted, alkoxy, aryloxy, acyloxy, arylthio, alkylthio, aryl-$S(O)_{1-2}$—, alkyl-$S(O)_{1-2}$—, hydroxyl, oxo, halogen, amino, oxime, —(C=O)—R, —(C=O)—O—R, thiocarboxyl, and amido;
the hydrocarbon chain —C($R_5$)—C($R_6$)—(CH)$_n$— of the ring-system adjacent the thiophene-ring is saturated or contains one or more double bonds between the carbon atoms;
n is an integer from 1 to 4, and
$R_5$ and $R_6$ are individually selected from the group consisting of hydrogen, alkyl, substituted alkyl, aryl or arylalkyl wherein the aryl group is optionally substituted, alkoxy, aryloxy, acyloxy, arylthio, alkylthio, aryl-$S(O)_{1-2}$—, alkyl-$S(O)_{1-2}$—, hydroxyl, oxo, halogen, amino, oxime, —(C=O)—R, —(C=O)—O—R, thiocarboxyl, and amido
wherein R may be hydrogen, alkyl, aryl, or aryl-($C_1$-$C_4$)-alkyl, both optionally substituted in the aryl group.

3. A method of treating a steroid hormone dependent disease or disorder, requiring the inhibition of the 17β-HSD type 1, 17β-HSD type 2 or 17β-HSD type 3 enzyme, wherein the steroid hormone dependent disease or disorder is selected from the group consisting of breast cancer, prostate carcinoma, ovarian cancer, uterine cancer, colon cancer, endometrial cancer, endometrial hyperplasia, endometriosis, uterine fibroids, uterine leiomyoma, adenomyosis, dysmenorrhea, menorrhagia, metrorrhagia, prostadynia, benign prostatic hyperplasia, acne, hirsutism, androgenic alopecia, precocious puberty, adrenal hyperplasia, polycystic ovarian syndrome, urinary dysfunction and osteoporosis, said method comprising administering to a patient suffering from one or more of the aforementioned steroid hormone dependent diseases or disorders an effective amount of a compound corresponding to formula (II)

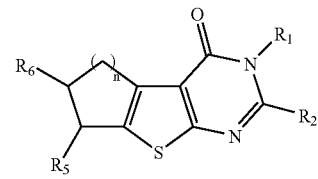

(II)

wherein
- $R_1$ and $R_2$ form together with their binding sites a cyclic 7-membered ring system, which is saturated or contains one or more double bonds between the ring atoms, and which ring contains zero N-atoms in addition to the nitrogen atom where $R_1$ is attached;
- wherein said ring is substituted with zero, one or two substituents independently selected from the group consisting of oxo, —CO—R, —CO—O—R, —O—R, and —$C_1$-$C_4$-alkyl, optionally substituted with —O—R, —S—R or —N(R)$_2$;
- the hydrocarbon chain —C($R_5$)—C($R_6$)—(CH)$_n$— of the ring-system adjacent the thiophene-ring is saturated or contains one or more double bonds between the carbon atoms;
- n is an integer from 1 to 4; and
- $R_5$ and $R_6$ are individually selected from the group consisting of hydrogen, oxo, halogen, —O—R', —S—R', —SO—R', —CO—R, —CO—O—R, —$C_1$-$C_4$-alkenyl or =$C_1$-$C_4$-alkylene, optionally substituted in the alkyl chain with —O—R, —S—R, —N(R)$_2$, —CO—R, or =N—O—R, wherein
    R represents hydrogen or $C_1$-$C_4$-alkyl; and
    R' represents hydrogen, $C_1$-$C_8$-alkyl, which can be linear, cyclic or branched; aryl-$C_1$-$C_4$-alkyl, or aryl.

* * * * *